United States Patent
Ryu et al.

(10) Patent No.: US 9,831,626 B2
(45) Date of Patent: Nov. 28, 2017

(54) BROADBAND LIGHT SOURCE AND OPTICAL INSPECTOR HAVING THE SAME

(71) Applicant: SAMSUNG ELECTRONICS CO., LTD., Suwon-si, Gyeonggi-do (KR)

(72) Inventors: Sung-Yoon Ryu, Hwaseong-si (KR); Woo-Seok Ko, Seoul (KR); Yu-Sin Yang, Seoul (KR); Sang-Kil Lee, Yongin-si (KR); Chung-Sam Jun, Suwon-si (KR); Seong-Jin Yun, Yongin-si (KR)

(73) Assignee: SAMSUNG ELECTRONICS CO., LTD., Suwon-Si, Gyeonggi-Do (KR)

( * ) Notice: Subject to any disclaimer, the term of this patent is extended or adjusted under 35 U.S.C. 154(b) by 56 days.

(21) Appl. No.: 14/872,228

(22) Filed: Oct. 1, 2015

(65) Prior Publication Data

US 2016/0097513 A1 Apr. 7, 2016

(30) Foreign Application Priority Data

Oct. 2, 2014 (KR) ........................ 10-2014-0133225

(51) Int. Cl.
*H01S 3/00* (2006.01)
*G01N 21/88* (2006.01)
*G01N 21/956* (2006.01)

(52) U.S. Cl.
CPC ....... *H01S 3/0071* (2013.01); *G01N 21/8806* (2013.01); *G01N 21/956* (2013.01)

(58) Field of Classification Search
CPC . H01S 3/0071; G01N 21/8806; G01N 21/956

USPC ................. 250/493.1, 453.11–455.11, 504 R
See application file for complete search history.

(56) References Cited

U.S. PATENT DOCUMENTS

| 6,819,423 | B2 | 11/2004 | Stehle et al. |
| 7,075,713 | B2 | 7/2006 | Arenberg |
| 7,164,144 | B2 | 1/2007 | Partlo et al. |
| 7,385,212 | B2 * | 6/2008 | Murakami .......... G03F 7/70033 250/492.1 |
| 7,705,331 | B1 * | 4/2010 | Kirk ..................... G01N 21/956 250/306 |
| 8,575,576 | B2 | 11/2013 | Solarz et al. |
| 8,692,986 | B2 | 4/2014 | Chuang et al. |
| 8,698,399 | B2 | 4/2014 | Bezel et al. |
| 2012/0147349 | A1 | 6/2012 | Van Dijsseldonk et al. |
| 2013/0169140 | A1 | 7/2013 | Ko et al. |
| 2013/0228695 | A1 | 9/2013 | Mizoguchi et al. |

FOREIGN PATENT DOCUMENTS

KR    10-2011-0049336 A    5/2011

* cited by examiner

*Primary Examiner* — Michael Maskell
(74) *Attorney, Agent, or Firm* — Lee & Morse, P.C.

(57) ABSTRACT

A broadband light source includes a first electrodeless lamp to generate first broadband light from plasma, a first elliptical reflector having first and second focuses, the first elliptical reflector enclosing a rear portion of the first electrodeless lamp positioned at the first focus of the first elliptical reflector such that the first broadband light is reflected from the first elliptical reflector toward a light collector as a collective light, a symmetrically curved reflector having a third focus, the symmetrically curved reflector positioned such that the third focus is coincident with one of the first and second focuses, and a laser irradiator to provide a laser beam to the first electrodeless lamp.

17 Claims, 8 Drawing Sheets

BROADBAND LIGHT SOURCE AND OPTICAL INSPECTOR HAVING THE SAME

CROSS-REFERENCE TO RELATED APPLICATION

Korean Patent Application No. 10-2014-0133225, filed on Oct. 2, 2014, in the Korean Intellectual Property Office, and entitled: "Broadband Light Source and Optical Inspector Having the Same," is incorporated by reference herein in its entirety.

BACKGROUND

1. Field

Example embodiments relate to a broadband light source and an optical inspector having the same, and more particularly, to a broadband light source generating a broadband light by using a laser produced plasma (LPP) system and an optical inspector having the same.

2. Description of the Related Art

As recent semiconductor devices tend to be stacked vertically to increase the degree of integration, various manufacturing defects internal to the devices, in addition to surface defects thereof, have increased. Thus, an optical inspecting system for inspecting the semiconductor devices needs inspection light having a wide wavelength range for inspecting various defects and a high intensity for reaching a sufficient depth within the devices.

A laser-produced plasma (LPP) system has been utilized as a light source for broadband light due to the simple control of the light intensity. The LPP light source has been applied to various light sources in semiconductor manufacturing processes such as photo lithography process as well as the optical inspection process.

SUMMARY

According to one or more exemplary embodiments, a broadband light source includes an electrodeless lamp to generate broadband light from plasma, an elliptical reflector having first and second focuses, the elliptical reflector enclosing a rear portion of the electrodeless lamp positioned at the first focus of the elliptical reflector such that the broadband light is reflected from the elliptical reflector toward a light collector as a collective light, a spherical reflector having a spherical center at which the electrodeless lamp is positioned, the spherical reflector enclosing a front portion of the electrodeless lamp such that the broadband light is reflected from the spherical reflector toward the elliptical reflector, the spherical reflector having a path hole through which the collective light passes toward the light collector, and a laser irradiator to provide a laser beam to the electrodeless lamp through the path hole of the spherical reflector to generate the plasma in the electrodeless lamp.

In an example embodiment, a mirror axis of the elliptical reflector may coincide with a major axis of the elliptical reflector, a first portion of the broadband light emitted from the rear portion of the electrodeless lamp may be reflected from the elliptical reflector toward the second focus of the elliptical reflector, a mirror axis of the spherical reflector may coincide with the major axis of the elliptical reflector, and a second portion of the broadband light emitted from the front portion of the electrodeless lamp may be reflected from the spherical reflector towards the elliptical reflector.

In an example embodiment, end portions of the elliptical and the spherical reflectors may be on a focal plane intersecting the first focus such that a maximal emitting angle $\alpha_{max}$ of the first portion of the broadband light is 90° clockwise or counterclockwise with respect to the major axis and a maximal focusing angle $\beta_{max}$ of the collective light is defined by equation (1) clockwise or counterclockwise with respect to the major axis, wherein $$\beta_{max} = \tan^{-1}\left(\frac{b\sqrt{1-\frac{c^2}{a^2}}}{2c}\right) \quad (1)$$

(wherein, 'a' denotes a distance of a prolate vertex, 'b' denotes a distance of an oblate vertex, and 'c' is a focal distance of the elliptical reflector from an origin of a Cartesian coordinate system).

In an example embodiment, the spherical reflector may have a radius R in a range of $$b\sqrt{1-\frac{c^2}{a^2}} \leq R \leq 2c.$$

In an example embodiment, the path hole may have a maximal cross sectional circle at which the spherical reflector intersects a beam flux of the collective light having the maximal focusing angle $\beta_{max}$.

In an example embodiment, the laser irradiator may include a laser source to generate the laser beam and an optical selector arranged on the major axis at a position that is spaced apart from the second focus by a gap distance and controlling an optical path of the laser and the collective light.

In an example embodiment, the laser source may be at the second focus and the light collector maybe spaced apart from the optical selector in a direction perpendicular to the major axis of the elliptical reflector.

In an example embodiment, the optical selector may include a dichromatic beam splitter that transmits the laser beam toward the elliptical reflector along the major axis and reflects the collective light toward the light collector in a direction perpendicular to the major axis.

In an example embodiment, the light collector may be at the second focus and the laser source may be spaced apart from the optical selector in a direction perpendicular to the major axis.

In an example embodiment, the optical selector may include a dichromatic beam splitter such that the laser beam perpendicular to the major axis is reflected toward the elliptical reflector along the major axis and the collective light passes through the optical selector toward the light collector along the major axis.

According to one or more exemplary embodiments, a broadband light source, includes a first light source to emit a first broadband light, the first light source having a first electrodeless lamp to generate the first broadband light from a first plasma and a first elliptical reflector that encloses the first electrodeless lamp positioned at a focal point of the first elliptical reflector, a second light source to emit a second broadband light, the second light source having a second electrodeless lamp to generate the second broadband light from a second plasma and a second elliptical reflector that encloses the second electrodeless lamp positioned at a focal point of the second elliptical reflector, a laser irradiator to irradiate a laser beam to the first and the second electrodeless lamps, thereby generating the first and the second plasma in the first and the second electrodeless lamps, respectively, and a path changer to change optical paths of the first and the second broadband lights and the laser such that the first and the second broadband lights travel toward a light collector as a collective light and the laser beam travels toward the first and the second reflectors, respectively.

In an example embodiment, the first elliptical reflector may have a first focus at which the first electrodeless lamp is positioned and a second focus, the first and second focuses defining a first major axis of the first elliptical reflector, the first elliptical reflector having a mirror axis corresponding to the first major axis, and the second elliptical reflector may have a third focus at which the second electrodeless lamp is positioned and a fourth focus, the third and fourth focuses defining a second major axis of the second elliptical reflector, the second elliptical reflector having a mirror axis corresponding to the second major axis.

In an example embodiment, the path changer may include a beam splitter located at a cross point of the first and the second major axes such that the path changer is spaced apart from the first and third focuses by a same gap distance, the broadband light source including an optical selector optically connected to both of the laser irradiator and the path changer, the optical selector to selectively transmit one of the laser beam and the collective light.

In an example embodiment, the laser irradiator may be at the fourth focus, the optical selector may be spaced apart from the fourth focus along the second major axis, and the light collector may be spaced apart from the optical selector in a direction perpendicular to the second major axis.

In an example embodiment, the optical selector may include a dichromatic beam splitter such that the laser beam travels through the dichromatic beam splitter along the second major axis toward the path changer to be split into two laser sub-beams that directed onto the first and the second elliptical reflectors, respectively, and the collective light is reflected from the dichromatic beam splitter toward the light collector in a direction perpendicular to the second major axis.

In an example embodiment, the light collector may be at the fourth focus, the optical selector may be spaced apart from the fourth focus along the second major axis, and the laser irradiator may be spaced apart from the optical selector in a direction perpendicular to the second major axis.

In an example embodiment, the optical selector may include a dichromatic beam splitter such that the laser beam is incident on the dichromatic beam splitter in a direction perpendicular to the second major axis and is reflected from the dichromatic beam splitter along the second major axis toward the path changer to be split into two laser sub-beams that are incident onto the first and the second elliptical reflectors, respectively, and the collective light travels through the dichromatic beam splitter along the second major axis toward the light collector.

In an example embodiment, the broadband light source may include a third elliptical reflector facing the first elliptical reflector and enclosing the second focus such that a mirror axis of the third elliptical reflector is a same as that of the first elliptical reflector.

In an example embodiment, the cross point of the first and second major axes may be spaced apart from the second focus and the fourth focus by a same gap distance such that a first portion of the first broadband light is reflected from the path changer toward the light collector as the collective light, a second portion of the first broadband light passes through the path changer toward the third elliptical reflector and is reflected again from the third elliptical reflector toward the path changer, a first portion of the second broadband light passes through the path changer toward the light collector as the collective light, a second portion of the second broadband light is reflected from the path changer toward the third elliptical reflector and is reflected again from the third elliptical reflector toward the path changer.

In an example embodiment, the broadband light source may include a first reflective film on a reflection surface of the first elliptical reflector and a second reflective film on a reflection surface of the second elliptical reflector.

According to one or more exemplary embodiments, a broadband light source includes a first electrodeless lamp to generate first broadband light from plasma, a first elliptical reflector having first and second focuses, the first elliptical reflector enclosing a rear portion of the first electrodeless lamp positioned at the first focus of the first elliptical reflector such that the first broadband light is reflected from the first elliptical reflector toward a light collector as a collective light, a symmetrically curved reflector having a third focus, the symmetrically curved reflector positioned such that the third focus is coincident with one of the first and second focuses, and a laser irradiator to provide a laser beam to the first electrodeless lamp.

In an example embodiment, an ellipsoid from which the elliptical reflector is cut out of and a shape from which the symmetrically curved reflector is cut out of may intersect.

In an example embodiment, the symmetrically curved reflector may be spherical reflector and the third focus may be coincident with the first focus.

In an example embodiment, the symmetrically curved reflector may be a second elliptical reflector having a fourth focus and the third focus, the third focus being coincident with the second focus, and the broadband light source may include a second electrodeless lamp to generate second broadband light from plasma, the second elliptical reflector enclosing a rear portion of the second electrodeless lamp positioned at the fourth focus of the second elliptical reflector, and a path changer to change the optical path of the second broadband light such that the second broadband light is focused at the third focus of the second elliptical reflector toward the light collector as collective light.

In an example embodiment, the path changer may direct some of the laser beam onto the first electrodeless lamp and some of the laser beam onto the second electrodeless lamp.

In an example embodiment, the broadband light source may include a third elliptical reflector facing the first elliptical reflector and enclosing the fourth focus such that a mirror axis of the third elliptical reflector is a same as that of the second elliptical reflector.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
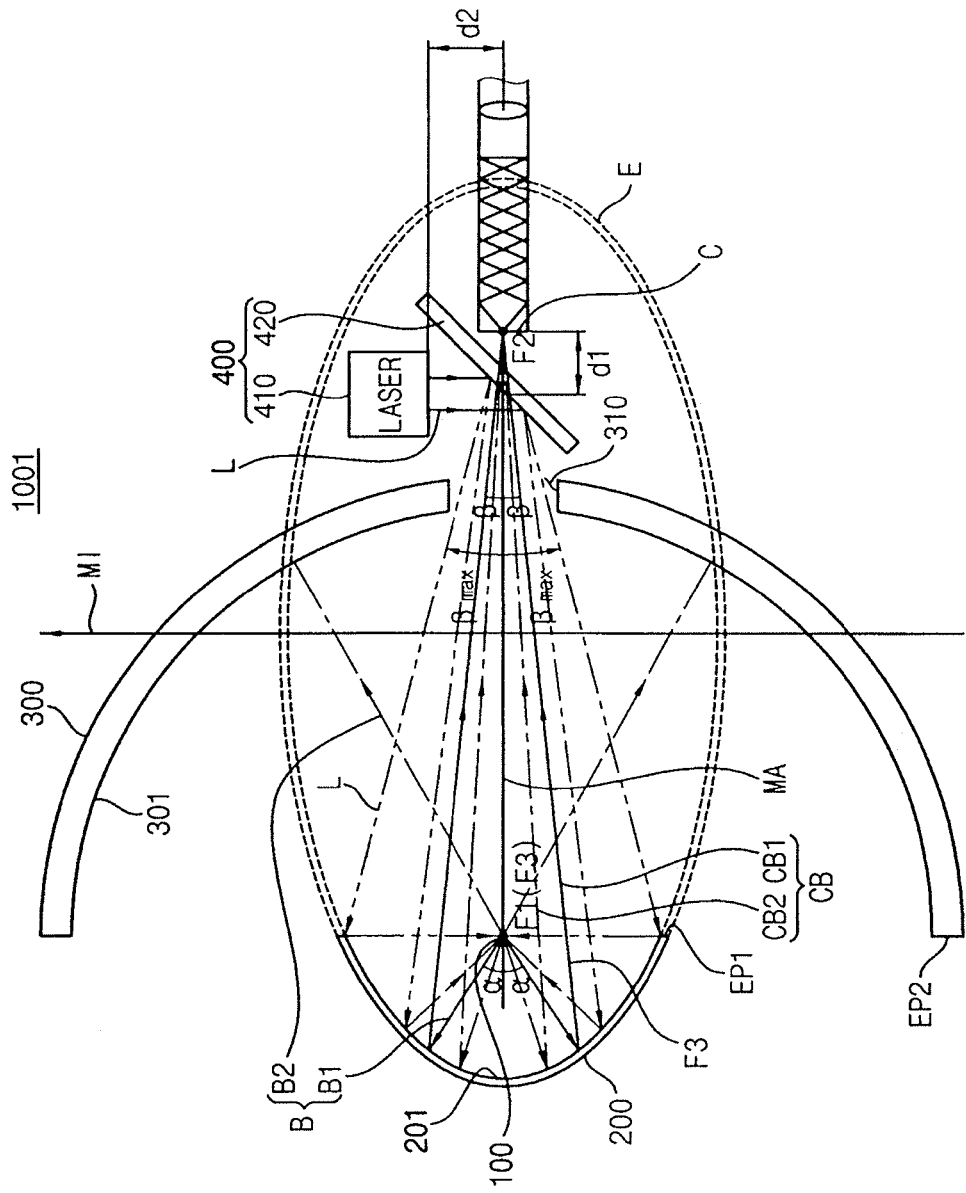
FIG. 1 illustrates a cross-sectional view of a broadband light source in accordance with an example embodiment.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Example embodiments may be described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will typically have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature, their shapes are not intended to illustrate the actual shape of a region of a device, and their shapes are not intended to limit the scope of the example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

As used herein, the term "spherical reflector" is to mean a mirror which has the shape of a piece cut out of a sphere. As used herein, the term "elliptical reflector" is to mean a mirror which has the shape of a piece cut out of an ellipsoid, e.g., a tri-axial ellipsoid or an oblate or prolate spheroid, and has two conjugate focuses. As used herein, the term "symmetrically curved reflector" is to mean a mirror that has the shape of a piece cut out of a closed quadratic shape having three axes of symmetry and defined by $$\frac{x^2}{a^2} + \frac{y^2}{b^2} + \frac{z^2}{c^2} = 1$$

where the coordinates (a,0,0), (0,b,0) and (0,0,c) are on the surface, e.g., either a spherical or an elliptical reflector.

Reference will now be made to example embodiments, which are illustrated in the accompanying drawings, wherein like reference numerals may refer to like components throughout.

FIG. 1 is a cross-sectional view illustrating a broadband light source in accordance with an example embodiment. Referring to FIG. 1, a broadband light source 1001 in accordance with the example embodiment may include an electrodeless lamp 100, an elliptical reflector 200 and a spherical reflector 300 facing each other, and a laser irradiator 400 irradiating a laser beam to the electrodeless lamp 100.

In an example embodiment, the electrodeless lamp 100 may generate broadband light B from plasma that may be produced using a laser beam. For example, the electrodeless lamp 100 may include a spherical glass lamp having a sufficiently small size and filled with gaseous mixtures.

The gaseous mixtures may have various seed materials including mercury (Hg) and various compositions and may be transformed into ionized gases in the electrodeless lamp 100. Thus, the broadband light B may be generated to have various wavelengths or bandwidths. For example, when an external power, e.g., radio frequency (RF) power, microwave power, and so forth, is applied to the electrodeless lamp 100, the electrodeless lamp 100 may be heated to a high temperature. Thus, seed materials including mercury (Hg) may be transformed into the ionized gases due to the evaporation of mercury (Hg), thereby forming a preliminary plasma in the electrodeless lamp 100.

Thereafter, a laser beam L may be irradiated onto the preliminary plasma in the electrodeless lamp 100 without the external power, thereby converting the preliminary plasma into a plasma of the gaseous mixture. Thus, when the state of the gaseous mixture degrades to the ground state from the excitation state, an electromagnetic wave is generated from the electrodeless lamp 100 as the broadband light B. Wavelengths of the electromagnetic wave may be varied according to the compositions of the gaseous mixture, so that the bandwidth of the broadband light may be varied due to the compositions of the gaseous mixture. Therefore, the electrodeless lamp 100 may function as a laser-produced plasma (LPP) light source.

Particularly, since the wavelength of the electromagnetic waves may be varied according to the compositions of the gaseous mixture in the electrodeless lamp 100, the bandwidth of the light generated from the electrodeless lamp may be broadened by varying the compositions of the gaseous mixtures. In the present example embodiment, the broadband light B may have the wavelength or the bandwidth of about 200 nm to about 500 nm.

Figure 8:
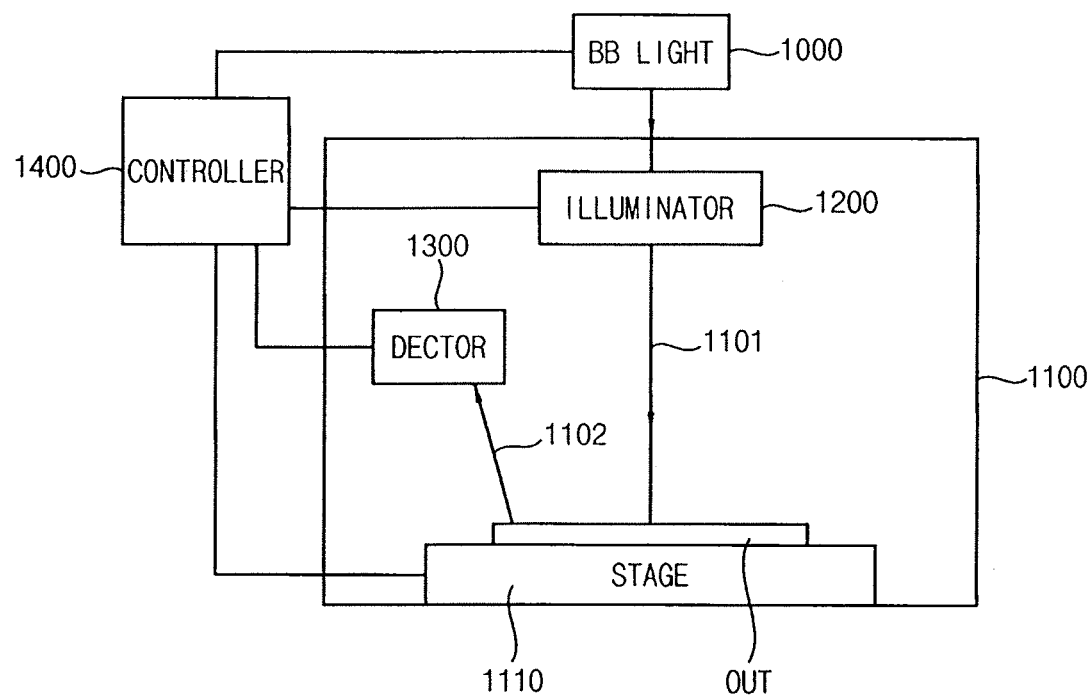
FIG. 8 illustrates a structural view of an optical inspector in accordance with an example embodiment.

Since the gaseous mixture is converted into the plasma state not by an internal energy in an electrode lamp, but by an external laser beam in the sufficiently small electrodeless lamp, the intensity of the broadband light B may be easily controlled by controlling the intensity of the external laser beam. In addition, the broadband light may be sufficiently prevented from being interrupted by an internal electrode when emitting from the lamp 100, because no internal electrode may be provided with the electrodeless lamp 100. Thus, as shown in FIG. 8, inspection light to be vertically illuminated onto an object under inspection may be easily generated from the broadband light source 1001. The higher the intensity of the vertical inspection light, the more the amount of the inspection light passes vertically into the object. Thus, the bridge defects or void defects in a deep portion of the object may be accurately and efficiently inspected or detected by an optical inspector including the broadband light source 1001.

The elliptical reflector 200 may be cut out of an ellipse E and may have first and second focuses F1 and F2. The elliptical reflector 200 may enclose, e.g., partially surround or overlap, a rear portion of the electrodeless lamp 100 positioned at the first focus F1 such that the broadband light B is reflected from the elliptical reflector 200 toward a light collector C as a collective light CB. Thus, the broadband light B emitting from the first focus F1 may be reflected from an elliptical reflection surface 201 of the elliptical reflector 200 toward the second focus F2.

In the present example embodiment, a major axis MA is defined by the first and second focuses F1 and F2 and a minor axis MI is perpendicular thereto. The elliptical reflector 200 may be arranged such that the first focus F1 is enclosed, e.g., partially surrounded or overlapped, by the elliptical reflector 200. The electrodeless lamp 100 may be positioned at the first focus F1 and, thus, may be enclosed, e.g., partially surrounded or overlapped, by the elliptical reflector 200. The emitting angles and the focusing angles discussed herein are relative to the major axis.

In the accompanying figures, the major axis MA and the minor axis MI may intersect at the origin point, i.e., (0, 0, 0) of a Cartesian coordinate system and may have a length of 2a and 2b, respectively. Thus, the ellipse E may have (−c, 0) and (c, 0) as the location coordinates of the first and second focuses F1 and F2, (−a, 0) and (a, 0) as the location coordinates of prolate vertexes and (0, −b) and (0, b) as the location coordinates of oblate vertexes in the Cartesian coordinate system.

Accordingly, the broadband light B output from the electrodeless lamp 100 at the first focus F1 is reflected from the elliptical reflector 200 toward the second focus F2. Hereinafter, the term 'front' denotes a side portion or a direction directed to the second focus F2 from the first focus F1 and the term 'rear' denotes a side portion or a direction directed to the first focus F1 from the second focus F2.

The elliptical reflector 200 may enclose, e.g., partially surround or overlap, the first focus F1 and the mirror axis of the elliptical reflector 200 may coincide with the major axis MA. Thus, the elliptical reflector 200 may concavely enclose, e.g., partially surround or overlap, the electrodeless lamp 100 at the first focus F1.

Particularly, end portions EP1 of the elliptical reflector 200 may be coplanar with a focal plane that intersects the first focus F1 and perpendicular to the mirror axis. That is, when the ellipse E having the first and the second focuses F1 and F2 is cut by a vertical line (perpendicular to the major axis MA) passing through the first focus F1, the elliptical reflector 200 corresponds to a rear portion of the ellipse E, so that the elliptical reflector 200 may enclose, e.g., partially surround or overlap, a rear portion of the electrodeless lamp 100.

Therefore, a first portion B1 of the broadband light B may be output onto the elliptical reflector 200 and a second portion B2 of the broadband light B may be output onto the spherical reflector 300 described in detail hereinafter. The second portion B2 of the broadband light B may be reflected from a spherical reflection surface 301 toward the elliptical reflection surface 201.

In the present example embodiment, a maximal emitting angle $\alpha_{max}$ of the first portion B1 of the broadband light B may be about 90° clockwise or counterclockwise with respect to the major axis MA. When the maximal emitting angle $\alpha_{max}$ is over about 90°, the broadband light B may be emitted toward the spherical reflector 300 as the second portion B2 of the broadband light B.

When the elliptical reflector 200 is cut out of the rear portion of the ellipse E such that the maximal emitting angle $\alpha_{max}$ of the first portion B1 of the broadband light B is over about 90°, a focusing angle β of a reflection light from the elliptical reflection surface 201 may be so great that the intensity of the light at the light collector C may be insufficient for the inspection to the object. The reflected light from the elliptical reflection surface 201 toward the second focus F2 is referred to as collective light CB that is directed to the light collector C and provided as inspection light for inspecting the object in an optical inspector. When the focusing angle β of the collective light CB is excessively large, the collective light CB may not pass through a path hole 310 of the spherical reflector 300, so that the amount of the collective light CB may be insufficient at the light collector C and the intensity of the collective light CB may be insufficient at the light collector C.

When the elliptical reflector 200 is cut out of the rear portion of the ellipse E such that the maximal emitting angle $\alpha_{max}$ of the first portion B1 of the broadband light B is less than about 90°, a large amount of the broadband light B may be dissipated without reflection from the elliptical reflection surface 201, thereby reducing optical efficiency of the electrodeless lamp 100 as well as the insufficient intensity of the collective light CB. When the broadband light B is emitted at the emitting angle between the maximal emitting angle $\alpha_{max}$ and 90°, the spherical reflector 300 may be arranged such that the broadband light B may be reflected from the spherical reflection surface 301. However, in such a case, the reflected light from the spherical reflection surface 301 may pass through the spherical center toward the opposite face of the spherical reflection surface 301. Thus, the reflected light may be endlessly reflected between the spherical reflection surfaces 301 opposite to each other with respect to the spherical center of the spherical reflector 300. As a result, even though the spherical reflector 300 may be provided in such a configuration that the dissipating light may be reflected from the spherical reflector 300, the broadband light B emitting at an angle between the maximal emitting angle and 90° may not be output to the light collector C.

For those reasons, the elliptical reflector 200 may be cut out of an ellipsoid having the major axis MA and minor axis MI by a focal plane at the first focus F1 in such a configuration that the electrodeless lamp 100 may be enclosed, e.g., partially surrounded or overlapped, by the elliptical reflector 200 having a maximal emitting angle $\alpha_{max}$ of the broadband light B may be about 90°.

Accordingly, the emitting angle $\alpha$ of the first portion B1 of the broadband light B may be less than or equal to about 90° and the emitting angle $\alpha$ of the second portion B2 of the broadband light B may be over about 90°. The collective light CB may include a first collective light CB1 formed from the first portion B1 of the broadband light B reflected from the elliptical reflector 200 and a second collective light CB2 formed from the second portion B2 of the broadband light B sequentially reflected from the spherical reflector 300 and the elliptical reflector 200.

When the first portion B1 of the broadband light B is emitted at an emitting angle of 0°, the broadband light B may be reflected from the elliptical reflector 200 on a horizontal surface including the major axis MA functioning as the mirror axis of the elliptical reflection surface 201, so that the first collective light CB1 travels toward the second focus F2 at a focusing angle of 0°. That is, the first portion B1 of the broadband light B having an emitting angle of 0° may be reflected from the elliptical reflector 200. Thus, the first collective light CB1 may travel toward the second focus F2 along the major axis MA at a focusing angle of 0°. As the emitting angle $\alpha$ of the first portion B1 of the broadband light B increases from 0°, the focusing angle $\beta$ of the first collective light CB1 may increase. Finally, when the first portion B1 of the broadband light B may be emitted at the maximal emitting angle $\alpha_{max}$ of 90°, the first collective light CB1 may be collected toward the second focus F2 at the maximal focusing angle $\beta_{max}$ defined by the following equation (1).

$$\beta_{max} = \tan^{-1}\left(\frac{b\sqrt{1-\frac{c^2}{a^2}}}{2c}\right) \quad (1)$$

Accordingly, when the broadband light B is incident onto the elliptical reflector 200 at an arbitrary emitting angle $\alpha$, a beam flux of the collective light B may constitute a side surface of a focusing cone FC having a vertex of the second focus F2 and a base circle of which the radius may be defined by tan $\alpha$. That is, the first portion B1 of the broadband light B emitting at an emitting angle of $\alpha$ may be reflected from the elliptical reflector 200 and the collective light CB may travel toward the second focus F2 along the side surface of the focusing cone.

The spherical reflector 300 may have the spherical center at which the electrodeless lamp 100 may be positioned and may enclose, e.g., partially surround or overlap, a front portion of the electrodeless lamp 100 such that the broadband light B may be reflected from the spherical reflector 300 toward the elliptical reflector 200. The spherical reflector 300 may also have a path hole 310 through which the collective light CB may pass toward the light collector C.

For example, the spherical reflector 300 may be arranged along the trajectory of a sphere having a center at the first focus F1 of the elliptical reflector 200 such that the focal plane passing the first focus F1 bisects the sphere. The spherical reflection surface 310 may have the same mirror axis as the elliptical reflector 200, so that the spherical reflector 300 may be a hemisphere spaced apart from the first focus F1 toward the second focus F2 and may face the elliptical reflector 200. That is, end portions EP2 of the spherical reflector 300 may also be coplanar with the focal plane that intersects the first focus F1 and the spherical reflector 300, and the elliptical reflector 200 may have a mirror axis in common with the major axis MA. The spherical reflector 300 may enclose, e.g., partially surround or overlap, a front portion of the electrodeless lamp 100. The spherical reflector 300 may have a third focus that coincides with the first focus f1.

In the present example embodiment, when the broadband light B is emitted at an emitting angle $\alpha$ greater than bout 90° from a front portion of the electrodeless lamp 100, the broadband light B (more specifically, the second portion B2 of the broadband light B) may be incident onto the spherical reflector 300 and may be reflected from the spherical reflection surface 301 toward the first focus F1. Then, the reflected light may pass reversely through the first focus F1 to be incident on the elliptical reflection surface 201 opposite to the spherical reflector 300. Finally, the reflection light from the spherical reflection surface 301 may be reflected again from the elliptical reflection surface 201 toward the second focus F2 as the second collective light CB2.

Figure 2:
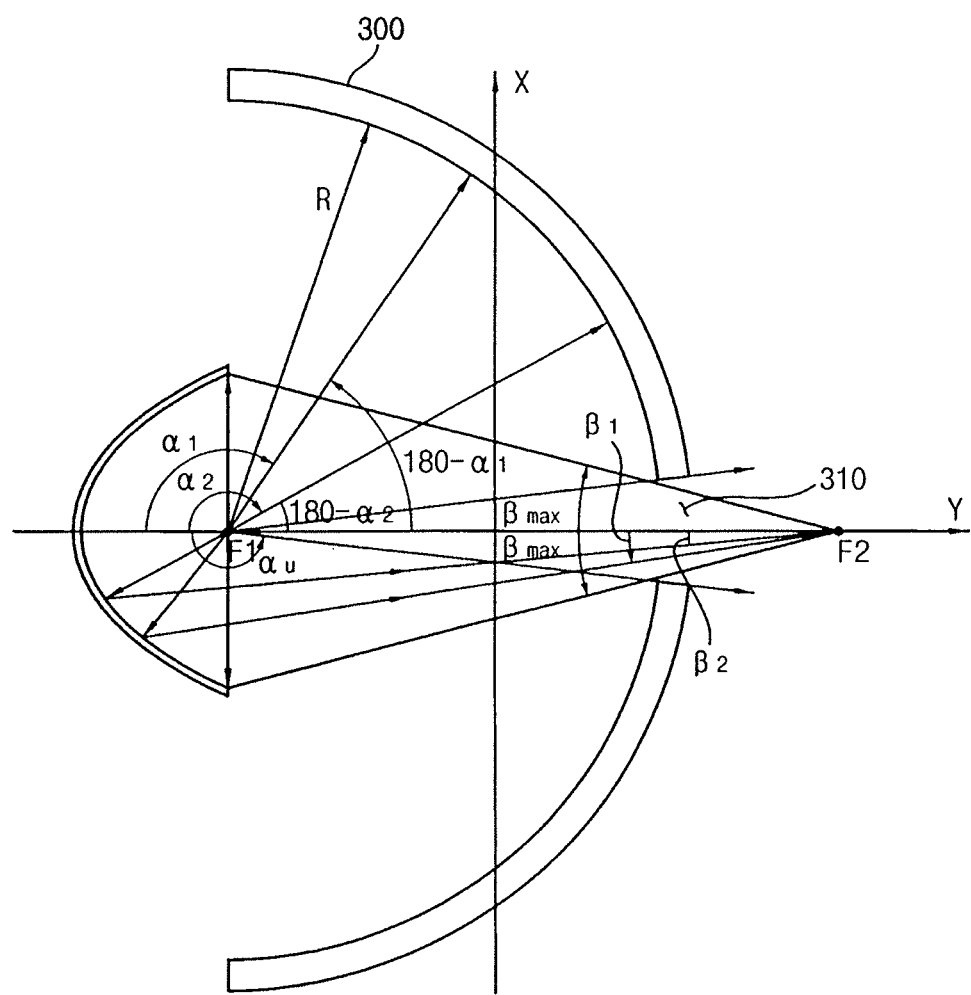
FIG. 2 illustrates a view of the relationship between the emitting angle α of the broadband light B and the focusing angle β of the collective light CB.

FIG. 2 illustrates a relationship between the emitting angle $\alpha$ of the broadband light B and the focusing angle $\beta$ of the collective light CB.

Referring to FIG. 2, the broadband light B emitted at a first emitting angle of $\alpha_1$, greater than about 90° from the electrodeless lamp 100 may be reflected from the spherical reflector 300 toward the elliptical reflector 200 and then may be reflected again from the elliptical reflector 200 at a first focusing angle $\beta_1$ toward the second focus F2. In addition, the broadband light B emitted at a second emitting angle of $\alpha_2$ greater than the first emitting angle $\alpha_1$ from the electrodeless lamp 100 may be reflected from the spherical reflector 300 toward the elliptical reflector 200 and then may be reflected again from the elliptical reflector 200 at a second focusing angle $\beta_2$ greater than the first focusing angle $\beta_1$ toward the second focus F2.

Since the second portion B2 of the broadband light B is reflected from the spherical reflector 300 to be incident onto the elliptical reflector 200 at a supplementary angle of the emitting angle $\alpha$, the focusing angle $\beta$ of the second collective light CB2 decreases as the emitting angle $\alpha$ of the second portion B2 of the broadband light B increases. Accordingly, the second portion B2 of the broadband light B may be sufficiently focused to the second focus F2 by the assembly of the spherical reflector 300 and the elliptical reflector 200, thereby increasing the intensity of the collective light C.

In contrast, the focusing angle β of the first collective light CB1 increases as the emitting angle α of the first portion B1 of the broadband light B increases, so that the first collective light CB1 may have the maximal focusing angle $β_{max}$ when the first portion B1 of the broadband light B is incident on the elliptical reflector 200 at the maximal emitting angle $α_{max}$. As a result, although the broadband light B may be emitted at various emitting angles α from the rear portion and front portion of the electrodeless lamp 100, the collective light CB may travel toward the second focus F2 below the maximal focusing angle $β_{max}$ corresponding to the maximal emitting angle of the first portion B1 of the broadband light B.

Accordingly, a large amount of the second portion B2 of the broadband light B may reach the light collector C at the focusing angle β below the maximal focusing angle $β_{max}$ while the second portion B2 of the broadband light B is wholly dissipated outwards in the conventional broadband light source, thereby increasing the intensity of the collective light CB at the light collector C.

When the second portion B2 of the broadband light B is emitted at an ultimate emitting angle $α_u$, the broadband light B may be dissipated outwards through the path hole 310 without any reflection from the spherical reflector 300.

In the present example embodiment, the path hole 310 may be arranged between the first and the second focuses F1 and F2, and thus the light collector C may be arranged at an exterior of the spherical reflector 300. Therefore, the radius R of the spherical reflector 300 may be varied from an optical path of the first portion B1 of the broadband light B at an emitting angle of 90° to a gap distance between the first and the second focuses F1 and F2. That is, the radius R of the spherical reflector 300 may be variable in a range of $$b\sqrt{1-\frac{c^2}{a^2}} \le R \le 2c.$$

Figure 3:
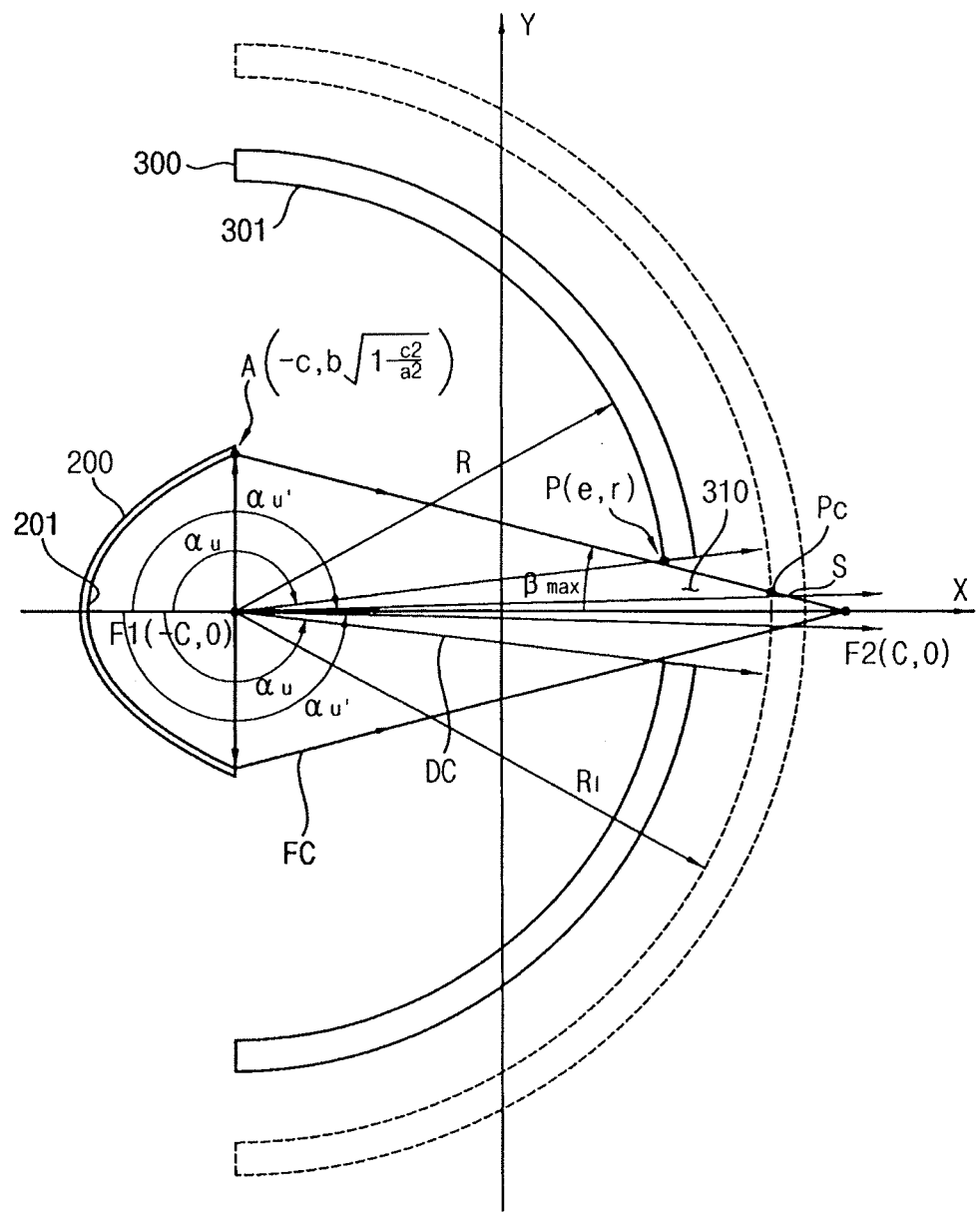
FIG. 3 illustrates a view of the structure of the path hole of the spherical reflector shown in FIG. 2.

FIG. 3 is a view illustrating the structure of the path hole of the spherical reflector shown in FIG. 2.

Referring to FIG. 3, a maximal focusing cone FC having a vertical angle of the maximal focusing angle $β_{max}$ may extend to the second focus F2 through the path hole 310 of the spherical reflector 300, thus the path hole 310 may have a cross sectional surface at which the maximal focusing cone FC intersects the sphere of the spherical reflector 300.

For example, a generator line S of the maximal focusing cone FC may cross a circle of the sphere of the spherical reflector 300 at a cross point P spaced apart from the major axis MA by a focusing gap distance r. Thus, the path hole 310 may be shaped into a cylinder having a radius corresponding to the focusing gap distance r and a height corresponding to a thickness of the spherical reflector 300.

In the present example embodiment, the generator line S may be mathematically expressed by a linear equation which passes a point A of the end portion EP1 of the elliptical reflector 200 and the second focus F2 as indicated by the following equation (2).

According to the Cartesian coordinate system shown in FIG. 3, the coordinates of the point A may be expressed as $$\left(-c, b\sqrt{1-\frac{c^2}{a^2}}\right)$$

and the coordinates of the second focus F2 may be expressed as (c, 0) and thus the linear equation may be expressed as follows.

$$y = -\frac{b}{2}\sqrt{1-\frac{c^2}{a^2}}\left(\frac{x}{c}-1\right) \quad (2)$$

In addition, a circle of the sphere of the spherical reflector 300 may be mathematically expressed by a circle equation of which the center may be located at the first focus F1 as indicated by the following equation (3).

In the same Cartesian Coordinate system shown in FIG. 3, since the coordinates of the first focus F1 may be expressed as (−c,0) and the radius of the spherical reflector 300 may be expressed as R, the equation of the circle of the spherical reflector 300 may be expressed as follows.

$$(x+c)^2+y^2=R^2 \quad (3)$$

The cross point P may satisfy both of the equation (2) and (3) and finding the cross point P may determine the position of the path hole 310 in the above coordinate system.

The x coordinate e of the cross point P may indicate the initial point of the path hole 310 on the major axis MA and the y coordinate r of the cross point P may indicate the radius r of the maximal cross sectional circle of the maximal focusing cone. That is, the path hole 310 may have a base circle having the radius r at the point (e, 0) and have a height corresponding to a thickness of the spherical reflector 300.

Therefore, the broadband light B emitting from the first focus F1 may be concentrated to the second focus F2 as long as the emitting angle α is within a range of about 0° to about $α_u$.

When the broadband light B is emitted from the first focus F1 at an emitting angle greater than the ultimate angle $α_u$, the broadband light B may be dissipated away through the path hole 310. Thus, a cone having a vertex at the first focus F1 and a base circle that passes the cross point P(e, r) may indicate a beam flux of the dissipating broadband light. Hereinafter, the cone indicating the beam flux of the dissipating broadband light is referred to as a dissipating cone DC.

Therefore, the larger the radius R of the spherical reflector 300, the smaller the radius r of the base circle of the path hole, a reducing the amount of the dissipated broadband light B, as illustrated in FIG. 3.

When the size of the spherical reflector 300 increases, the radius R of the spherical reflector 300 increases to an increased radius Ri and the cross point P may also be changed to a changed cross point Pc. As a result, the ultimate emitting angle $α_u$ may be increased to an increased ultimate angle $α_{u'}$ that may be larger than the ultimate emitting angle $α_u$ and the vertex angle and the base circle of the dissipating cone DC may also be reduced, thereby reducing the amount of the dissipating broadband light B.

In such a case, since the path hole 310 is located at a front of the second focus F2, the radius R of the spherical reflector 300 may also be less than 2c corresponding to the gap distance of the first and the second focuses F1 and F2.

For example, the laser irradiator 400 may irradiate a laser beam L to the electrodeless lamp 100 through the path hole 310 of the spherical reflector 300, thereby generating the plasma in the electrodeless lamp 100. In the present example embodiment, the laser irradiator may include a laser source 410 generating the laser beam and an optical selector 420 arranged on the major axis MA at a position spaced apart from the second focus F2 by a gap distance. The optical selector 420 may control optical paths of the laser beam L and the collective light CB.

The laser source 410 may include a laser generator arranged outside of the spherical reflector 300, and thus the laser beam L may be irradiated to the electrodeless lamp 100 from the exterior of the spherical reflector 300 through the path hole 310. The laser beam L may convert the ionized gases in the electrodeless lamp 100 into a plasma state. In the present example embodiment, the laser beam L may generate a plasma area at a central portion of the electrodeless lamp 100 in a range of about 400 μm to about 500 μm.

A preliminary energy provider may be further provided in the electrodeless lamp 100 for generating the ionized gases in the electrodeless lamp 100. For example, an external power source, e.g., an RF power, a microwave power, and so forth may be applied to the electrodeless lamp 100 in advance and the ionized gases may be under high pressure as a preliminary plasma state before the irradiation of the laser beam L.

The laser beam L may be irradiated onto the elliptical reflector 200 and may be reflected to the electrodeless lamp 100 positioned at the first focus F1. Thus, the laser beam L may be focused to a central portion of the electrodeless lamp 100 corresponding to the first focus F1.

In the present example embodiment, the laser beam L may travel to the elliptical reflector 200 from the laser source 410 through the path hole 310 along a reverse path of the collective light CB. That is, the focusing cone FC, the beam flux of the collective light CB, may function as a laser cone LC, a beam flux of the laser beam L.

The laser beam L may need to be irradiated at a position optically equivalent to the second focus F2 in order for the laser beam L to be reflected from the elliptical reflector 200 to the first focus F1 at which the electrodeless lamp 100 is positioned.

In an example embodiment, the light collector C may be positioned at the second focus F2 and the laser source 410 may be vertically spaced apart from the major axis MA. Thus the laser beam L may travel in parallel with the minor axis MI from the laser source 410 and then be redirected toward the elliptical reflector 200 along the major axis MA, to thereby form the beam flux of the laser beam L in the laser cone LC.

For that reason, the optical selector 420 may be arranged at an intersection of the major axis MA and an optical path of the laser beam L to guide the laser beam L to the path hole 310. Particularly, the optical paths of the laser beam L and the collective light CB may be reverse to each other, so that the optical selector 420 may control the laser beam L to travel through the path hole 310 toward the elliptical reflector 200 and simultaneously control the collective light CB to travel toward the light collector C.

Figure 4:
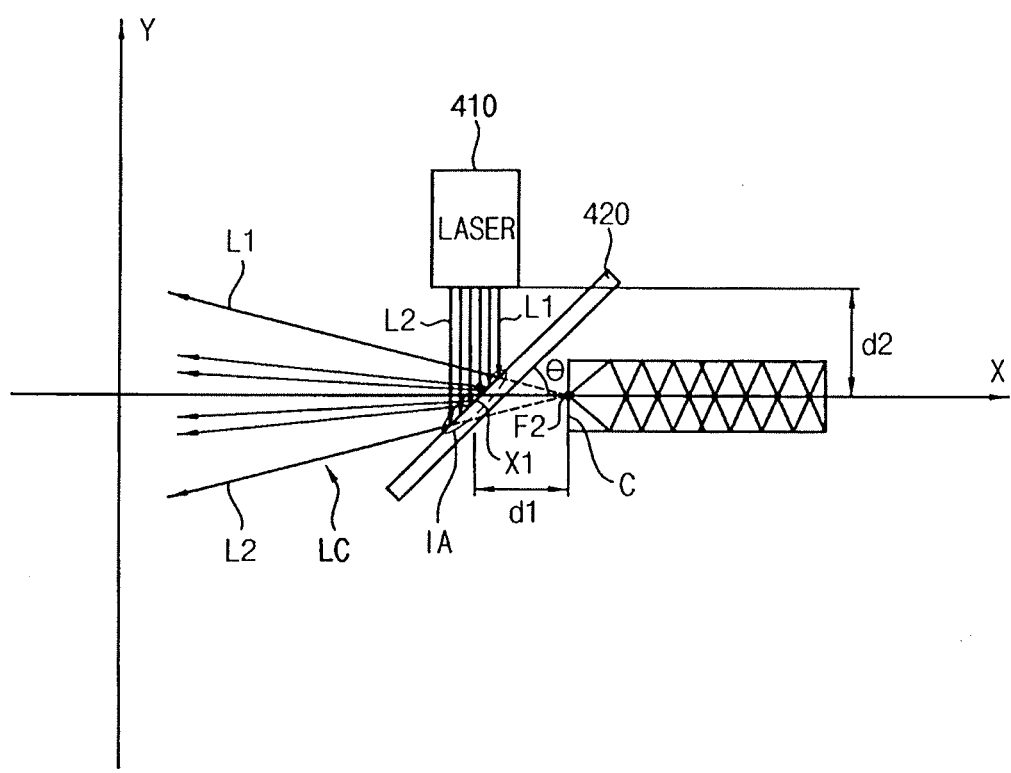
FIG. 4 illustrates a structural view of the laser irradiator of the broadband light source shown in FIG. 1.

FIG. 4 illustrates a structural view of the laser irradiator of the broadband light source shown in FIG. 1. Referring to FIG. 4, the optical selector 420 may intersect the major axis MA at a first position x1 spaced apart from the second focus F2 by a first gap distance d1 at an angle θ with respect to the major axis MA. The laser source 410 may be spaced apart from the first position x1 by a second gap distance d2 in a direction perpendicular to the major axis MA.

The laser beam L may be irradiated to the first position x1 of the major axis MA from the laser source 410 in parallel with the minor axis MI and then may be reflected from the optical selector 420 at the first position x1 toward the path hole 310. When the first gap distance d1 is equal to the second gap distance d2, the laser beam L reflected from the first position x1 may be optically equivalent to a laser beam irradiated from the second focus F2 along the major axis MA. In the same way, a first portion L1 of the laser beam L, which may be irradiated onto an upper portion of the optical selector 420 with respect to the first position x1, may also be reflected from the optical selector 420 above the major axis MA and may be optically equivalent to a laser beam irradiated from the second focus F2 in the same direction. A second portion L2 of the laser beam L, which may be irradiated onto a lower portion of the optical selector 420 with respect to the first position x1, may also be reflected from the optical selector 420 below the major axis MA and may be optically equivalent to a laser beam irradiated from the second focus F2 in the same direction. That is, the laser beam L may be irradiated to an irradiation area IA of the optical selector 420, which may include the upper portion and the lower portion symmetrical with respect to the first position x1, and may reflected toward the path hole 310 as if the laser source 410 were located at the second focus F2.

Thus, the irradiation area IA may correspond to an intersection area of the focusing cone FC and the optical selector 420 and the beam flux of the laser beam L that may be irradiated onto the irradiation area IA of the optical selector 420 may be distributed on the laser cone LC as if the vertex point were located at the second focus F2. That is, the laser beam L may be reflected from the irradiation area IA of the optical selector 420 as if the laser beam L were irradiated from the second focus F2.

Therefore, the laser beam L reflected from the irradiation area IA of the optical selector 420 may reach the elliptical reflection surface 201 and may be focused to the first focus F1 at which the electrodeless lamp 100 is positioned. Since the irradiation area IA corresponds to the intersection area of the focusing cone FC and the optical selector 420, the size of the irradiation area IA of the optical selector 420 may be varied according to the angle θ of the optical selector 420 relative to the major axis MA.

When the optical selector 420 is between the second focus F2 and the path hole 310, the optical selector 420 may need to transmit the collective light CB. Thus, the optical selector 420 may include a beam splitter from which the laser beam L may be reflected and simultaneously through which the collective light may pass. For example, the optical selector 420 may include a dichromatic beam splitter for simultaneously performing transmission and reflection of light according to the wavelength thereof.

In such a case, the laser beam L may be reflected from the dichromatic beam splitter to the elliptical reflector 200 and the collective light CB may simultaneously pass through the dichromatic beam splitter toward the light collector C since the wavelength of the laser beam L may be different from that of the collective light CB.

While the present example embodiment discloses that the light collector C is at the second focus F2 and the laser source 410 is spaced apart from the major axis MA, any other modifications of the laser source 410 and the light collector C may be used as long as the first gap distance d1 is equal to the second gap distance d2, such that both the laser source 410 and the light collector C effectively appear to be at the second focus F2.

For example, the laser source 410 may be arranged at the second focus F2 and the light collector C may be spaced apart from the major axis MA. When the laser source 410 is at the second focus F2 and the light collector C is spaced apart from the first position x1 of the major axis MA in parallel with the minor axis MI, the laser beam L may pass through the irradiation area IA of the optical selector 420 to travel toward the elliptical reflector 200, while the collective light CB may be reflected from the irradiation area IA of the optical selector 420 to travel in a direction perpendicular to the major axis MA to thereby reach the light collector C.

The laser beam L may be continuously provided to the electrodeless lamp 100 and, thus, the plasma may be continuously generated in the electrodeless lamp 100 as long as the broadband light source 1001 is operated. Particularly, the laser beam L may be controlled to have sufficient intensity and wavelength for converting the gaseous mixtures into an excited state of the plasma. Thus, the second portion B2 of the broadband light B may be prevented from being absorbed for generating the plasma when the second portion B2 of the broadband light B is reflected from the spherical reflector 300 to pass through the first focus F1 at which the electrodeless lamp 100 is positioned. Therefore, the second portion B2 of the broadband light B may reach the elliptical reflector 200 without any dissipation in the electrodeless lamp 100.

According to the above example embodiment of the broadband light source, a large amount of the second portion B2 of the broadband light B emitted toward the front side of the electrodeless lamp 100 may be reflected to the elliptical reflector 200 at the rear portion of the electrodeless lamp 100, so that the second portion B2 of the broadband light B may also be collected by the light collector C and a larger amount of the broadband light may reach the light collector C. Particularly, the laser beam L for generating the plasma may be continuously provided to the electrodeless lamp 100 from the exterior of the spherical reflector 300 as long as the broadband light source is operated. Thus, the second portion B2 of the broadband light B may be prevented from being absorbed or dissipated into the electrodeless lamp 100 for generating the plasma when the second portion B2 of the broadband light B is reflected from the spherical reflector 300 to pass through the first focus F1 toward the elliptical reflector 200. Accordingly, the intensity of the broadband light may sufficiently increase and thus the intensity of an inspection light of an optical inspector including the broadband light source 1001 may also increase.

Figure 5:
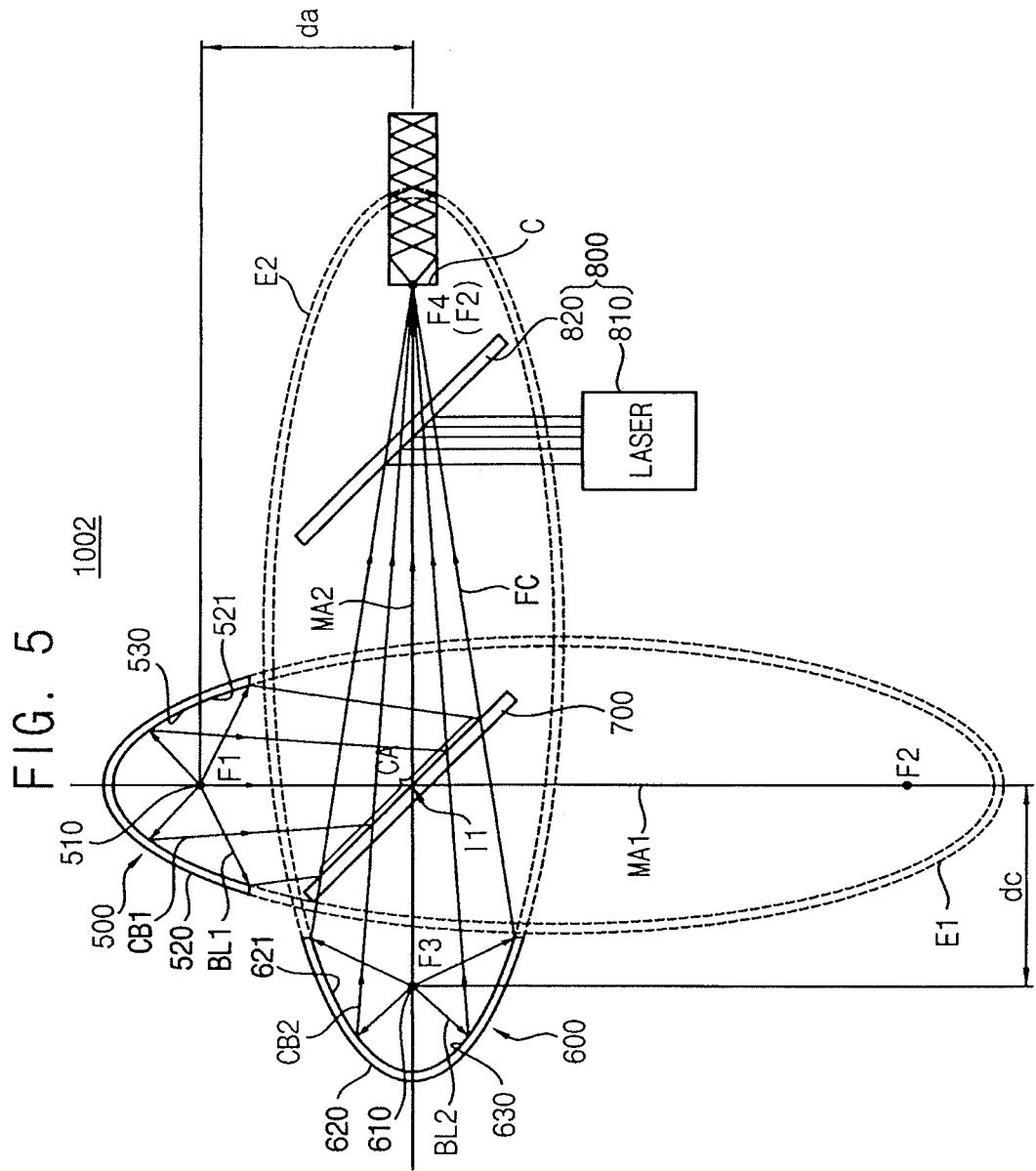
FIG. 5 illustrates a cross-sectional view of a broadband light source in accordance with an example embodiment.
Figure 6:
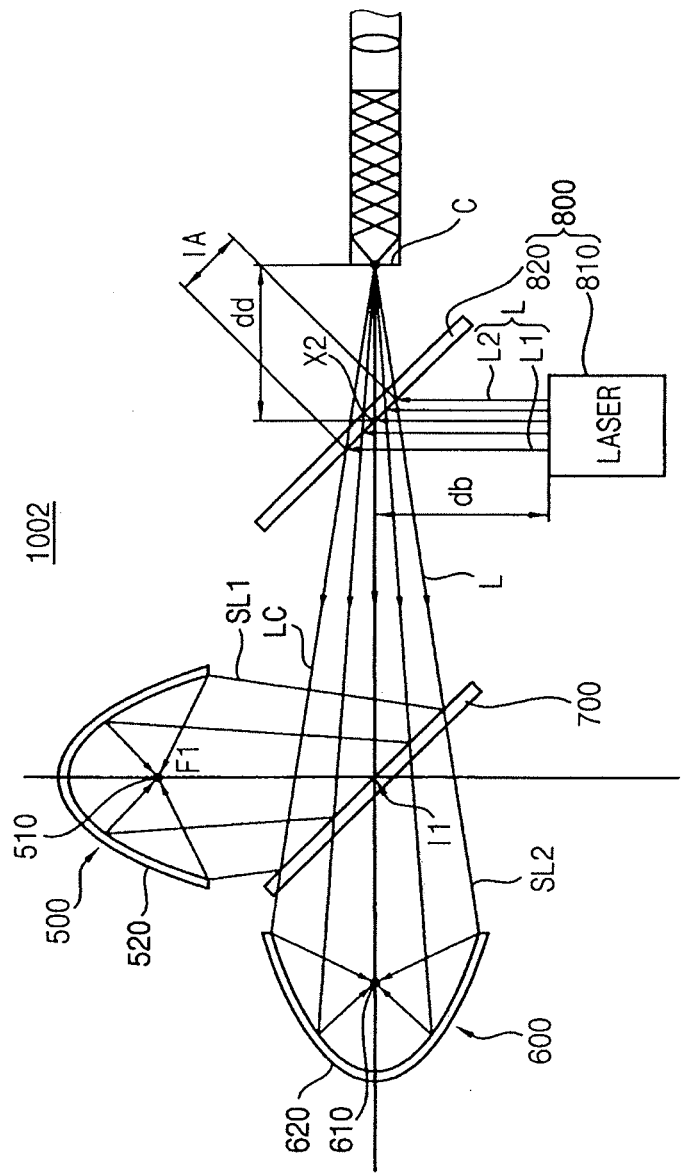
FIG. 6 illustrates a view of an optical path of the laser of the broadband light source shown in FIG. 5.

FIG. 5 is a cross-sectional view illustrating a broadband light source in accordance with an example embodiment. FIG. 6 is a view illustrating an optical path of the laser of the broadband light source shown in FIG. 5.

Referring to FIGS. 5 and 6, a broadband light source 1002 in accordance with the example embodiment may include a first light source 500 emitting a first broadband light BL1, a second light source 600 emitting a second broadband light BL2, a laser irradiator 800 irradiating a laser beam L to the first and second light sources 500 and 600, a path changer 700 changing optical paths of the first and second broadband lights BL1 and BL2, and of the laser beam L.

For example, the first light source 500 may include a first electrodeless lamp 510 generating the first broadband light BL1 from a first plasma and a first elliptical reflector 520 may be cut out of a first ellipse E1 and may enclose, e.g., partially surround or overlap, the first electrodeless lamp 510 positioned at a first focal point F1 of the first elliptical reflector 520. The second light source 520 may include a second electrodeless lamp 610 generating the second broadband light BL2 from a second plasma and a second elliptical reflector 620 that may be cut out of a second ellipse E2 and may enclose, e.g., partially surround or overlap, the second electrodeless lamp 620 positioned at a third focal point F3 of the second elliptical reflector 620.

A first major axis MA1 may be defined by the first and second focuses F1 and F2 and a mirror axis of the first elliptical reflector 520 may coincide with the first major axis MA1. In the same way, a second major axis MA2 may be defined the third and fourth focuses F3 and F4 and a mirror axis of the second elliptical reflector 620 may coincide with the second major axis MA2. The first and second elliptical reflectors 510 and 610 may have the same geometric design such that the second focus F2 coincides with the fourth focus F4 when the light from the first light source 500 is redirected by the path changer 700.

The first and the second electrodeless lamps 510 and 610 may be filled with different gaseous mixtures. Thus, the compositions of the plasma may be different between the first and the second electrodeless lamps 510 and 610. The first broadband light BL1 may be generated from the laser-produced plasma in the first electrodeless lamp 510 and the second broadband light BL2 may be generated from the laser-produced plasma in the second electrodeless lamp 610. Therefore, the first and the second broadband lights BL1 and BL2 may have different wavelengths due to the composition difference of the plasma in each electrodeless lamp 510 and 610. For example, the mixture gases of each electrodeless lamp 510 and 610 may be selected and controlled in such a way that the first broadband light BL1 may have a wavelength range of about 200 nm to about 350 nm and the second broadband light BL2 may have a wavelength range of about 300 nm to about 500 nm, e.g., the wavelength ranges may be different, but may partially overlap.

The first broadband light BL1 output from the first electrodeless lamp 510 may be reflected from the first elliptic reflector 520 and may be focused to the second focus F2. Here, due to the path changer 700, the second focus F2 may coincide with the fourth focus F4. In an example embodiment, the first elliptical reflector 520 may concavely enclose, e.g., partially surround or overlap, the first electrodeless lamp 510 and the first electrodeless lamp 510 may be arranged at the first focus F1 of the first ellipse E1. Thus, the first broadband light BL1 generated from the first electrodeless lamp 510 may be reflected from the first elliptical reflector 520 toward the second focus F2 as a first collective light CB1.

In the same way, the second broadband light BL2 emitting from the second electrodeless lamp 610 may be reflected from the second elliptical reflector 620 and may be focused to the fourth focus F4. In an example embodiment, the second elliptical reflector 620 may concavely enclose, e.g., partially surround or overlap, the second electrodeless lamp 610 and the second electrodeless lamp 610 may be arranged at the third focus F3 of the second ellipse E2. Thus, the second broadband light BL2 generated from the second electrodeless lamp 610 may be reflected from the second elliptical reflector 620 toward the fourth focus F4 as a second collective light CB2.

In a modified example embodiment, first and second reflective films 530 and 630 may be further provided, e.g., coated, on first and second reflection surfaces 521 and 621, thereby increasing the reflection efficiency of the first and the second elliptical reflectors 510 and 610.

The reflection characteristics of the reflective films 530 and 630 may be varied according to light absorption and refraction properties of the material. Thus, when some wavelengths of the first and the second broadband lights BL1 and BL2 may be absorbed or refracted from the reflective films 530 and 630, respectively, the reflection characteristics of the reflective films 530 and 630 may be reduced.

Thus, the first broadband light BL1 may have a first bandwidth and may be sufficiently reflected from the first reflective film 530 with minimal absorption and refraction of the wavelength within the first bandwidth, thereby sufficiently increasing the reflection efficiency of the first broadband light BL1 at the first elliptical reflector 520. The second broadband light BL2 may have a second bandwidth and may be sufficiently reflected from the second reflective film 630 with minimal absorption and refraction of the wavelength within the second bandwidth, thereby sufficiently increasing the reflection efficiency of the second broadband light BL1 at the second elliptical reflector 620.

When a single broadband light having both of the first and the second bandwidths is generated from a single electrodeless lamp, the reflective film on a single elliptical reflector may be not be optimized to reflect the broadband light with minimal absorption and refraction of the wavelength within both of the first and the second bandwidths. Thus, the greater the number of the bandwidths of the broadband light incident on a single reflector, the larger the amount of the absorbed or refracted broadband light. That is, when the broadband light having a wide bandwidth is reflected from a single elliptical reflector, some wavelengths of the broadband light may be absorbed into or refracted from the reflector. Thus, a relatively large amount of the broadband light may be dissipated away by the reflector, thereby decreasing the intensity of the broadband light at the light collector C.

However, when a plurality of broadband lights having a respective bandwidth is individually reflected from a plurality of elliptical reflectors, respectively, properties of the individual reflective films on the corresponding elliptical reflectors may be controlled to reflect the respective broadband light with minimal absorption and refraction of the wavelength within the respective bandwidth, thereby minimizing the dissipation of the broadband light and increasing the intensity of the broadband light at the light collector C.

In the present example embodiment, since the first broadband light BL1 having the first bandwidth may be reflected from the first elliptical reflector 520 and the second broadband light BL2 having the second bandwidth may be reflected from the second elliptical reflector 620, the first reflective film 530 may be controlled to maximize the reflection efficiency of the first broadband light BL1 with minimal absorption and refraction of the wavelength within the first bandwidth and the second reflective film 630 may be controlled to maximize the reflection efficiency of the second broadband light BL2 with minimal absorption and refraction of the wavelength within the second bandwidth.

While the present example embodiment discloses a pair of the light sources 500 and 600 in the broadband light source 1002, a plurality of the light sources each of which may have a respective electrodeless lamp and a respective elliptical reflector coated with a respective reflective film may be provided with the broadband light source 1002, thereby minimizing the partial dissipation of the broadband light and maximizing the intensity of the broadband light at the light collector C.

In the present example embodiment, since, without the path changer 700, the first collective light CB1 may travel to the second focus F2 and the second collective light CB2 may travel to the fourth focus F4, the optical paths of the first and the second collective lights CB1 and CB2 may be changed by the path changer 700 and the first and the second collective lights CB1 and CB2 may be focused to a single point of the light collector C, i.e., the fourth focus F4.

The path changer 700 may change optical paths of the first and the second collective lights CB1 and CB2, and of the laser beam L such that the first and the second collective lights CB1 and CB2 travel toward the light collector C and the laser beam L travels toward the first and the second reflectors 510 and 610, respectively. The path changer 700 may be arranged in various configurations according to the positions of the first and the second light sources 500 and 600, the position of the light collector C, and the position of the laser irradiator 700.

For example, when the first and the second major axes MA1 and MA2 are perpendicular to each other and the light collector C is at the fourth focus F4, the first collective light CB1 may be vertically reflected to the fourth focus F4 and the second collective light CB2 may pass straight forward to the fourth focus F4, i.e., without any change of the optical path thereof.

Thus, the path changer 700 may selectively transmit or reflect incident light. In the present example embodiment, the path changer 700 may include a beam splitter for transmitting or reflecting the incident light, preferably, a 50:50 beam splitter in which the incident light may be divided into a reflected light and a transmitted light of equal portions.

When the first collective light CB1 is reflected to the path changer 700 by the first elliptical reflector 520, 50% of the first collective light CB1 may be reflected to the fourth focus F4 by the path changer 700 and 50% of the first collective light CB1 may be transmitted toward the second focus F2 by the path changer 700. Therefore, the 50% of the first collective light CB1 transmitted by the path changer 700 may be dissipated, i.e., is not focused to the light collector C.

In the same way, when the second collective light CB2 may be reflected to the path changer 700 by the second elliptical reflector 620, 50% of the second collective light CB2 may be transmitted toward the fourth focus F4 by the path changer 700 and 50% of the second collective light CB2 may be reflected to the second focus F2 by the path changer 700. Therefore, 50% of the second collective light CB2 reflected from the path changer 700 may be dissipated, i.e., is not focused to the light collector C.

In such a case, the path changer 700 may be spaced apart from the first focus F1 at which the first electrodeless lamp 510 is positioned by a first gap distance da and simultaneously spaced apart from the third focus F3 at which the second electrodeless lamp 610 is positioned by a third gap distance dc that may be substantially the same as the first gap distance da. Thus, 50% of the first collective light CB1 that is reflected from the path changer 700 may be sufficiently focused to the fourth focus F4 together with 50% of the second collective light CB2 that passes through the path changer 800.

Therefore, when a central portion of the path changer 700 is positioned at an intersection of cross point I1 of the first and the second major axes MA1 and MA2, the first and the third focuses F1 and F3 may be spaced apart from the cross point I1 by the same gap distance, the first collective light CB1 reflected from the path changer 700 may be focused to the fourth focus F4 as if the first collective light CB1 were emitted from the third focus F3. In addition, the second collective light CB2 reflected from the path changer 700 may be focused to the second focus F2 as if the second collective light CB2 were emitted from the first focus F1.

For example, the path changer 700 may be a plate positioned at an angle with respect to the first and the second major axes MA1 and MA2. The beam flux of the first and the second collective lights CB1 and CB2 may be incident onto a changing area CA of the path changer 800, and the reflected portion of the first collective light CB1, which may be reflected from the changing area CA of the path changer 800, and the transmitting portion of the second collective light CB2, which may pass through the changing area CA of the path changer 700, may focused to the fourth focus F4. Therefore, the reflected portion of the first collective light CB1 and the transmitted portion of the second collective light CB2 may constitute a focusing cone FC having a base area corresponding to the changing area CA and a height corresponding to a distance between the cross point I1 and the fourth focus F4. Since the changing area CA of the path changer 700 is slanted at an angle with respect to the first major axis MA1, the focusing cone FC may be formed as a slant cone in which the base plane may be slanted with respect to the height of a cone.

That is, the reflected portion of the first collective light CB1 and the transmitted portion of the second collective light CB2 may be focused to the fourth focus F4 and be collected to the light collector C along the focusing cone FC. Accordingly, the first and the second electrodeless lamps 510 and 610, even though positioned at the first and the third focuses F1 and F3, respectively, may be optically equivalent to a single virtual electrodeless lamp positioned at the third focus F3.

The laser irradiator 800 may irradiate the laser beam L to the first and the second electrodeless lamps 510 and 610, thereby generating the first and the second plasma in the first and the second electrodeless lamps 510 and 610, respectively. For example, the laser irradiator 800 may include a laser source 810 generating the laser beam L and an optical selector 820 arranged on the second major axis MA2 at a position that may be spaced apart from the fourth focus F4 by a fourth gap distance dd and controlling an optical path of the laser beam L and the first and the second collective lights CB1 and CB2.

The laser source 810 may include a laser generator outside the first and second light sources 500 and 600. Thus, the laser beam L may be guided to each of the first and the second electrodeless lamps 510 and 610 from the exterior of the first and the second light sources 500 and 600. The laser beam L may transform the ionized gases in each of the first and the second electrodeless lamps 510 and 610 into first and second plasma states, respectively. In the present example embodiment, the laser beam L may generate a plasma area at a central portion of each of the electrodeless lamps 510 and 610 in a range of about 400 μm to about 500 μm.

The laser beam L may be simultaneously irradiated onto each of the first and the second reflection surfaces 521 and 621 and may be reflected to the first and the second electrodeless lamps 510 and 610 at the first focus F1 and the third focus F3, respectively. Thus, the laser beam L may be simultaneously focused to a central portion of the first and the second electrodeless lamps 510 and 610, respectively.

In the present example embodiment, the laser beam L may travel to both of the first and the second elliptical reflector 520 and 620 from the single laser source 810 along a reverse path of the first and the second collective lights CB1 and CB2. Thus, the laser beam L may pass toward along a reverse direction of the focusing cone FC and then may be split toward the first and the second elliptical reflector 520 and 620, respectively. The split laser beam L may be reflected from the first and the second elliptical reflector 520 and 620, respectively, and may be focused to the first and the second electrodeless lamps 510 and 610, respectively. Therefore, the slanted focusing cone FC, the beam flux of the collective light CB focusing to the fourth focus F4, may function as a laser cone LC, a beam flux of the laser beam L irradiating from the fourth focus F4 or the position optically equivalent to the fourth focus F4.

The laser beam L may be generated from the single laser source 810 and then may be incident to the path changer 700 by which the laser beam L may be split into first and second split lasers SL1 and SL2 that may be irradiated onto the first and the second elliptical reflectors 520 and 620, respectively.

In the present example embodiment, the path changer 700 may divide the laser beam L by the same optical density just like the first and the second broadband lights BL1 and BL2, so that the laser beam L may be split into the first and second split lasers SL1 and SL2 having the same optical density. Thus, about 50% of the optical amount of the laser beam L may be reflected from the path changer 700 to the first elliptical reflector 520 as the first split laser SL1 and the rest about 50% of the optical amount of the laser beam L may be transmitted by the path changer 700 to the second elliptical reflector 620 as the second laser SL2. Therefore, the first and second plasmas in the first and the second electrodeless lamps 510 and 610 may be produced by the same intensity of the split lasers SL1 and SL2.

The first split laser SL1 may be irradiated at a position optically equivalent to the second focus F2 such that the first split laser SL1 may be reflected from the first elliptical reflector 520 to the first focus F1 at which the first electrodeless lamp 510 is positioned. In the same way, the second split laser SL2 may be irradiated at a position optically equivalent to the fourth focus F4 such that the second split laser SL2 may be reflected from the second elliptical reflector 620 to the third focus F3 at which the second electrodeless lamp 610 is positioned.

In an example embodiment, the light collector C may be positioned at the fourth focus F4 and the laser source 810 may be vertically spaced apart from the second major axis MA2, thus the laser beam L may travel in parallel with the first major axis MA1 from the laser source 810 and then be reflected toward the path changer 700, to thereby form the beam flux of the laser beam L in the laser cone LC.

The optical selector 820 may be arranged at an intersection area of the second major axis MA2 and an optical path of the laser beam L for guiding the laser beam L to the path changer 700. Particularly, the optical paths of the laser beam L and the first and the second collective lights CB1 and CB2 may be reverse to each other. Thus, the optical selector 820 may control the laser beam L to travel toward the path changer 700 and simultaneously control the first and the second collective lights CB1 and CB2 to travel toward the light collector C.

As shown in detail in FIG. 6, the optical selector 820 may intersect the second major axis MA2 at a second position x2 spaced apart from the fourth focus F4 by a fourth gap distance dd at an angle θ with respect to the second major axis MA2. The laser source 810 may be spaced apart from the second position x2 by a second gap distance db in a direction perpendicular to the second major axis MA2.

The laser beam L may be irradiated to the second position x2 of the second major axis MA2 from the laser source 810 in a direction perpendicular to the second major axis MA2 and then may be reflected from the optical selector 820 at the second position x2 toward the path changer 700. When the fourth gap distance dd is equal to the second gap distance db, the laser beam L reflected from the second position x2 may be optically equivalent to a laser beam irradiated from the fourth focus F4 along the second major axis MA2.

In the same way, a first portion L1 of the laser beam L, irradiated onto an upper portion of the optical selector 820 with respect to the second position x2, may also be reflected from the optical selector 820 above the second major axis MA2 and optically equivalent to a laser beam that may be irradiated from the fourth focus F4 in the same direction. A second portion L2 of the laser beam L irradiated onto a lower portion of the optical selector 820 with respect to the first position x1 is reflected from the optical selector 820 below the second major axis MA2, i.e., is optically equivalent to a laser beam irradiated from the fourth focus F4 in the same direction. That is, the laser beam L may be irradiated to an irradiation area IA of the optical selector 820 having the upper portion and the lower portion symmetrical with respect to the second position x2, and is reflected toward the path changer 700 as if the laser source 810 were located at the fourth focus F4.

Thus, the irradiation area IA may correspond to an intersection area of the slanted focusing cone FC and the optical selector 820 and the beam flux of the laser beam L that may be irradiated onto the irradiation area IA of the optical selector 820 may be distributed on the laser cone LC as if the vertex point were located at the fourth focus F4. That is, the laser beam L may be reflected from the irradiation area IA of the optical selector 820 as if the laser beam L were irradiated from the fourth focus F4.

Therefore, the laser beam L reflected from the irradiation area IA of the optical selector 820 may reach the changing area CA of the path changer 700 and may be split into the first and the second split laser beams SL1 and SL2 passing toward the first and the second elliptical reflector 520 and 620, respectively. The first and the second split laser beams SL1 and SL2 may be focused to the first and the third focuses F1 and F3 at which the first and the second electrodeless lamps 510 and 610 are positioned, respectively. Since the irradiation area IA may correspond to the intersection area of the slanted focusing cone FC and the optical selector 820, the size of the irradiation area IA of the optical selector 820 may be varied according to the slant angle θ of the optical selector 820.

When the optical selector 820 is between the fourth focus F4 and the path changer 700, the optical selector 820 may need to transmit the first and the second collective lights CB1 and CB2. Thus, the optical selector 820 may include a beam splitter from which the laser beam L may be reflected and simultaneously through which the collective lights CB1 and CB2 may pass. For example, the optical selector 820 may include a dichromatic beam splitter for simultaneously performing transmission and reflection of light according to the wavelength thereof.

In such a case, the laser beam L is reflected from the dichromatic beam splitter to the changing area CA of the path changer 700 and the first and the second collective lights CB1 and CB2 simultaneously pass through the dichromatic beam splitter toward the light collector C since the wavelength of the laser beam L may be different from that of the collective lights CB1 and CB2.

The laser source 810 and the light collector C may be exchanged with each other as long as the second gap distance db and the fourth gap distance dd are the same without any modifications of the optical characteristics of the first and the second collective lights CB1 and CB2.

When the laser source 810 is at the fourth focus F4 and the light collector C is spaced apart from the second position x2 by the second gap db distance perpendicular to the second major axis MA2, the laser beam L may pass through the optical selector 820 and be irradiated to the path changer 700 and the first and the second collective lights CB1 and CB2 may be reflected from the optical selector 820 to thereby focused to the light collector C.

While the present example embodiments disclose that the light collector C may be positioned at the fourth focus F4 and the laser irradiator 800 may be arrange around the second major axis MA2, any other modifications would be allowable to the light collector C and the laser irradiator 800 as long as the optical characteristics of the laser beam L and the broadband lights BL1 and BL2 may be unchanged. For example, the light collector C would be positioned at the second focus F2 and the laser irradiator 800 would be arranged around the first major axis MA1.

In a modified example embodiment, an additional reflector may be further provided with the broadband light source 1002 for preventing the dissipation of the broadband lights BL1 and BL2 due to the reflection and transmission of the path changer 700.

Figure 7:
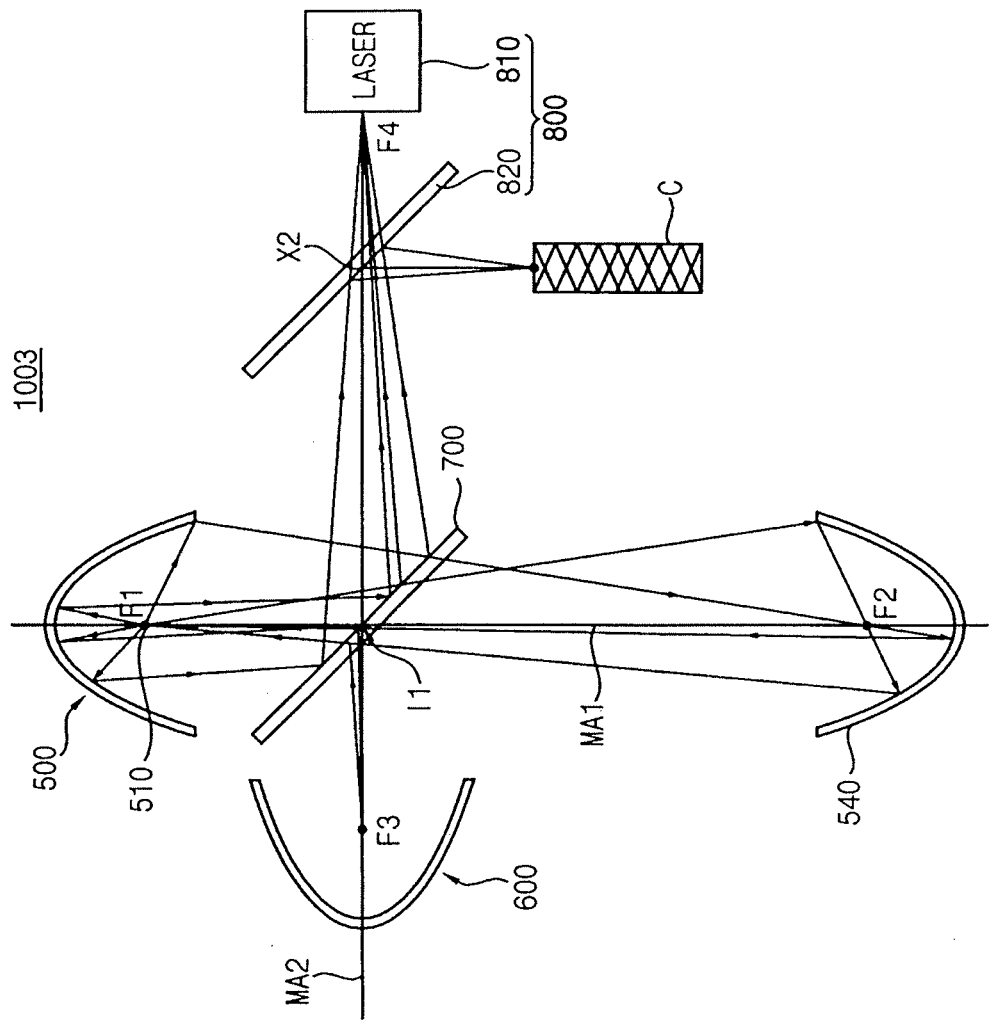
FIG. 7 illustrates a cross-sectional view of a broadband light source in accordance with an example embodiment.

FIG. 7 is a cross-sectional view illustrating a broadband light source in accordance with a third example embodiment. In FIG. 7, the third example embodiment of the broadband light source may have substantially the same structures as the broadband light source shown in FIG. 5, except for a third elliptical reflector and and a position of the laser source and the optical selector. Thus, in FIG. 7, the same reference numerals denote the same elements in FIG. 5 and any further detailed descriptions on the same elements will be omitted.

Referring to FIG. 7, a broadband light source 1003 in accordance with a third example embodiment may further include a third elliptical reflector 540 that may be partially cut out of the first ellipse E1 such that the second focus F2 may be enclosed, e.g., partially surround or overlap, with the third elliptical reflector 540 and face the first elliptical reflector 520 along the first major axis MA1.

Particularly, when a mirror axis of the third elliptical reflector 540 coincides with the first major axis MA1 of the first ellipse E1, the third elliptical reflector 540 is opposite to the first elliptical reflector 520 along the first major axis MA1 in an optical viewpoint.

In addition, the gap distance between the cross point I1 and the second focus F2 may be substantially the same as the gap distance between the cross point I1 and the fourth focus F4.

Thus, when the first collective light CB1 having an optical amount or an intensity of $\phi_1$ may be incident to the path changer 700, such as an 50:50 beam splitter, about 50% of the first collective light CB1 having an optical amount of about $\frac{1}{2}\phi_1$ may be reflected from the path changer 700 to thereby reach the light collector C and the rest 50% of the first collective light CB1 having an optical amount of about $\frac{1}{2}\phi_1$ may pass through the path changer 700 to be focused at the second focus F2.

Then, the first collective light CB1 passing through the second focus F2 may be reflected from the third elliptical reflector 540 toward the first focus F1 of the first ellipse E1, to thereby reach again the path changer 700. Particularly, the first collective light CB1 reflected from the third elliptical reflector 540 may be optically equivalent to a light generating from the second focus F2.

The first collective light CB1 reflected from the third elliptical reflector 540 may also be split again by the 50:50 beam splitter of path changer 700. Thus, about 50% of the first collective light CB1 reflected from the third elliptical reflector 540 and having an optical amount of about ¼ϕ₁ may be reflected from the path changer 700 to thereby reach the second elliptical reflector 620 and the rest 50% of the first collective light CB1 reflected from the third elliptical reflector 540 and having an optical amount of about ¼ϕ₁ may pass through the path changer 700 and be focused to the first focus F1.

Since the second reflective film 630 on the second elliptical reflector 620 may be configured to optimally reflect the second broadband light BL2 having the second bandwidth, the first broadband light BL1 having the first bandwidth may be absorbed to or refracted from the second reflective film 630. Thus, the first collective light CB1 having an optical amount of about ¼ϕ₁ and reflected from the path changer 700 to the second elliptical reflector 620 may be dissipated by absorption and refraction at the second elliptical reflector 620. In contrast, the first collective light CB1 having an optical amount of about ¼ϕ₁ and passing through the path changer 700 to the first elliptical reflector 520 may be reflected again from the first elliptical reflector 520 and split again by the path changer 700 into the first collective light having an optical amount of about ⅛ϕ₁ and reflected toward the light collector C and the first collective light having an optical amount of about ⅛ϕ₁ and passing toward the third elliptical reflector 540.

Therefore, the first collective light CB1 having the optical amount of ϕ₁ may be repeatedly and infinitely reflected between the first and the third elliptical reflectors 520 and 540 facing each other along the mirror axis thereof in such a manner that the optical amount of the first collective light CB1 that reaches the light collector C may be reduced to about $(½)^{2n-1}ϕ_1$ at every time of reflection from the first elliptical reflector 520. That is, when the first collective light CB1 is reflected a first time (first order) from the first elliptical reflector 520 after being output from the first electrodeless lamp 510, the optical amount of the first collective light CB1 at the light collector C is reduced to about ½ϕ₁. In addition, when the first collective light CB1 is reflected a second time (second order) from the first elliptical reflector 520 after being reflected from the third elliptical reflector 540, the optical amount of the first collective light CB1 at the light collector C is reduced to about ⅛ϕ₁.

Accordingly, a total optical amount of the first collective light CB1, which may be collected at the light collector C in the broadband light source 1003 including the first and the third elliptical reflectors 520 and 540, may be calculated as the following equation (4).

$$\varphi_{total,1} = \sum_{n=1}^{\infty} \left(\frac{1}{2}\right)^{2n-1} \varphi_1 = \frac{2}{3}\varphi_1 \tag{4}$$

(wherein, $n$ is an integer denoting a reflection order at the first elliptical reflector)

In the same way, the second collective light CB2 may also be repeatedly and infinitely reflected between the second and the third elliptical reflectors 620 and 540 due to the optical path changer 700. When the second collective light CB2 is generated from the second electrodeless lamp 610 at the third focus F3 with an initial optical amount of ϕ₂ and is repeatedly and infinitely reflected between the second and the third elliptical reflectors 620 and 540, a total optical amount of the second collective light CB2 is collected at the light collector C in the broadband light source 1003 including the second and the third elliptical reflectors 620 and 540, may be calculated as the following equation (5).

$$\varphi_{total,2} = \sum_{n=1}^{\infty} \left(\frac{1}{2}\right)^{2n-1} \varphi_2 = \frac{2}{3}\varphi_2 \tag{5}$$

(wherein, $n$ is an integer denoting a reflection order at the second elliptical reflector)

As a result, the optical amount of the collective lights CB1 and CB2 may be sufficiently increased due to the third elliptical reflector 540 at the light collector C. For example, the total optical amount of the first collective light CB1 at the light collector C may be about 67% of the initial optical amount in the broadband light source 1003 while the total optical amount of the first collective light CB1 at the light collector C may be about 50% of the initial optical amount in the broadband light source 1002, so that the light intensity may increase as much as about 34% at the light collector C.

In addition, the focusing angle β of the collective lights CB1 and CB2 may be gradually reduced as the reflection order may increase at the first and the second elliptical reflectors 520 and 620 due to geometrical characteristics of the elliptical reflection of light. For example, the focusing angle β of the second order beam of the first collective light CB1 may be smaller than that of the first order beam of the first collective light CB1. Therefore, the intensity of the collective light CB1 and CB2 may sufficiently increase at small focusing angles around 0°, and thus an inspection light may be vertically illuminated onto an object with high intensity when the collective lights CB1 and CB2 may be used as the inspection light in an optical inspector including the broadband light source.

The above intensity increase may occur to the laser beam L as well as the broadband lights BL1 and BL2.

The laser beam L may be generated from the laser source 810 and may be incident to the path changer 700 with an initial optical amount or an initial intensity of L₁₀, and then may be irradiated onto the first and the second elliptical reflectors 520 and 620, respectively, with an intensity of about ½L₀.

Some of the laser beam L may be utilized for generating the plasma in each electrodeless lamp and residuals of the laser beam L may be reflected again from the elliptical reflectors to thereby be incident again to the path changer 700. Supposing that the conversion efficiency of the laser beam L be ϵ less than 1, the residuals of the laser beam L may be again incident to the path changer 700 with the reduced optical amount of about ½(1−ϵ)L₀. In such a case, the residuals of the laser beam L may partially pass through the optical path 700 and is reflected from the third elliptical reflector 540, and then reflected from the third elliptical reflector 540. Thus, some of the residuals of the laser beam L may be irradiated again to the first and the second elliptical reflectors 520 and 620, and then may be provided again to the first and the second electrodeless lamps 510 and 610. That is, some of the laser beam L, which may not contribute the generation of the plasma, may be recycled and utilized for generating the plasma in each electrodeless lamp by the third elliptical reflector 540.

Thus, the operation efficiency of the laser beam L may increase as much as the recycling optical amount of the laser beam L to thereby decrease the driving power of the laser source 810.

According to the example embodiments of the broadband light source, a plurality of the broadband lights having respective bandwidths may be generated from a plurality electrodeless lamps, respectively, and may be focused to a single light collector by using a path changer for changing optical paths of each broadband light. Therefore, the bandwidth of the broadband light may be easily broadened.

Particularly, a reflective film for maximizing the reflection efficiency of the broadband light within a respective bandwidth may be provided with each of the elliptical reflectors, thus the dissipation such as the absorption and the refraction of the respective broadband light may be minimized at each elliptical reflector. Accordingly, the bandwidth of the broadband light source may be sufficiently broadened while minimizing the dissipation of the broadband light.

In addition, an additional reflector may be further provided with the broadband light source in such a manner that the broadband light or the laser passing through the path changer may be reflected again to the elliptical reflectors, thereby increasing the intensity of the collective light and the laser.

FIG. 8 is a structural view illustrating an optical inspector in accordance with an example embodiment. The optical inspector is disclosed as an example of an optical system including the broadband light sources. However, the optical inspector is just illustrative of the optical system and is not to be construed as limiting thereof and rather the optical system may be used in various optical apparatuses and devices, e.g., a photolithography apparatus, an imaging apparatus, and so forth.

Referring to FIG. 8, an optical inspector 2000 in accordance with an example embodiment may include a broadband (BB) light source 1000 generating broadband light, an illuminator 1200 receiving light from the broadband light source 1000 and converting the broadband light into an inspection light and illuminating the inspection light to an object under test (OUT) under inspection on a stage 1110, a detector 1300 detecting a detection light from the object corresponding to the inspection light, and a controller 1400 controlling the broadband light source 1000, the illuminator 1200 and the detector 1300 and inspecting defects of the object by analyzing the inspection light and the detection light.

For example, the broadband light source 1000 may include at least one electrodeless lamp that filled with gaseous mixtures. An external laser may be applied to the electrodeless lamp for converting the gaseous mixtures into plasma and the broadband light may be generated from the electrodeless lamp in the plasma conversion of the gaseous mixtures, so that the electrodeless lamp may function as a laser-produced plasma (LPP) light source.

In FIG. 8, the optical inspector 2000 may include any one of the broadband light sources 1001 to 1003 for generating the broadband light, and thus any further detailed descriptions on the same elements will be omitted.

The object under test (OUT) may be loaded into a chamber 1100 and an optical inspection to the OUT may be performed by using the broadband light in the chamber 1100. Particularly, the OUT may be secured to a bottom of the chamber 1100 and the inspection light 1101 may be illuminated onto the OUT. Then, the detection light 1102 may be detected from the OUT corresponding to the inspection light 1101 and may be analyzed together with the inspection light 1101, thereby inspecting and detecting defects from a surface and an interior of the OUT.

The stage 1110 supports the OUT at a bottom portion and the illuminator 1200 for illuminating the inspection light 1101 may be provided to a top portion of the OUT opposite to the stage 1110. The stage 1110 may be controlled in a three-dimensional space by a driving unit, e.g., a robot arm. Thus, the stage 1110 may be controlled to locate at an optimal position with respect to the illuminator 1200. The driving unit of the stage 1110 may be controlled by the controller 1400 together with the illuminator 1200.

The illuminator 1200 may convert the collective light CB, the broadband light collected at the light collector C of the broadband light source 1000, into the inspection light 1101 for inspecting the OUT and may control the optical characteristics of the inspection light 1101. For example, the illuminator 1200 may transform a point light of the collective light CB into a surface light of the inspection light 1101.

In the present example embodiment, the illuminator 1200 may include a lens assembly including a rod lens and an objective lens. The rod lens may be connected with the light collector C of the broadband light sources shown in FIGS. 1 to 3, so that the broadband light BL may be collected at the light collector C as the collective light CB and the collective light CB may be transformed into the inspection light for inspecting the OUT by the lens assembly of the illuminator 1200. The collective light C, which may be focused as spherical point light, may be modified into a surface light shaped into a plate by the rod lens. Then, the inspection light may be focused onto the OUT on the stage 1110 by the objective lens and a plurality of optical instruments.

For example, the optical instruments may include an aperture and a neutral density (ND) filter for controlling an illuminating amount of the inspection light and a band filter and a polarizer for selecting an optimal bandwidth of the broadband light for the OUT. Accordingly, the inspection light may be optimized for the OUT on the stage 1110 in an optical viewpoint by the illuminator 1200. For example, the OUT may include minute pattern structures for semiconductor devices.

The detector 1300 may detect the detection light generated from the OUT and optically treat the detection light, thereby generating an inspection image illustrating the defects of the OUT. For example, the detector 1300 may include an optical receiver (not shown) for receiving the detection light and an image processor (not shown) for generating the inspection image from the detection light. The inspection light may be reflected, refracted. or diffracted from the OUT and, thus, the detection light may include reflected light, refracted light, and/or diffracted light of the inspection light.

The detector 1300 may be controlled by the controller 1400 and thus may be operated together with the illuminator 1200 and the stage 1110. While the present example embodiment discloses that the detector 1300 is within the chamber 1100, any other modifications may be allowable as long as the detector may sufficiently detect the detection light and may be controlled by the controller 1400. For example, the detector 1300 may be arranged at an exterior of the chamber 1100 and may detect the detection light via a lens system.

The controller 1400 may be electrically connected with the broadband light source 1000, the stage 1110, the illuminator 1200, and the detector 1300, so that the broadband light source 1000, the stage 1110, the illuminator 1200, and the detector 1300 may be systematically operated by the controller 1400 for conducting the optical inspection to the OUT. Particularly, the inspection image may visually illustrate the position and size of the defects of the OUT.

Therefore, the inspection light 1101 having the different bandwidths optimized for the corresponding defects may be illuminated to the OUT and the inspection image may be generated from the detection light that may be generated from the OUT corresponding to the inspection light, thus the defects may be accurately and clearly found from the defect image. For example, the size and positions of the void defects and the bridge defects may be accurately and clearly found in a multilayered pattern structure of semiconductor devices by the optical inspector 2000.

When the broadband light source generates a plurality of broadband lights having different bandwidths, the defects of the OUT may be detected by the respective inspection light having a bandwidth optimal for detecting the corresponding defect. Thus, different various defects of which the defect characteristics, such as size, shape, location, and so forth, may be different from one another may be simultaneously and accurately detected in the optical inspector 2000. Further, a larger amount of the broadband light may be focused to the light collector C and, thus, the intensity of the inspection light may be sufficiently increased. Therefore, a deep defect, which may be located at a deep position from a surface of the OUT, may be accurately and clearly inspected and detected by the optical inspector 2000.

Accordingly, the broadband light source 1000 of the optical inspector 2000 may have a wide-range bandwidth and a high intensity, so that various defects of the OUT may be accurately detected even though the characteristics and locations of the defects may be different from one another in the OUT.

By way of summation and review, in general, an LPP light source used for the inspection light for an optical inspecting system includes a plasma light source for generating broadband light using the laser-produced plasma and an elliptical collecting mirror for focusing the broadband light onto a rod lens. The elliptical collecting mirror may be arranged only at the rear side of the plasma light source. Thus, a front portion of the broadband light cannot reach the rod lens of the optical inspector, which may reduce the intensity of the inspection light. In addition, as the line width of the semiconductor devices has been reduced and the number of the vertical stack increases, the locations of the defects has been widely distributed and the sizes and shapes of the defects has been diversified.

In contrast, in accordance with one or more embodiments of the broadband light source and the optical inspector including the same, a large amount of the dissipated light may be collected at the light collector by using a spherical reflector, thereby increasing an intensity of the inspection light that may be illuminated onto the rod lens. In addition, in accordance with one or more embodiments of the broadband light source and the optical inspector including the same, a plurality of the broadband lights having a respective bandwidth may be combined into a single inspection light of the optical inspector, thus the bandwidth of the inspection light may be easily broadened. Therefore, various defects of the OUT may be accurately detected by the optical inspector.

The present example embodiments of the broadband light source may be applied to various optical systems or optical apparatuses in which the LPP is used for generating the light. For example, the broadband light source may also be applied to a photolithography apparatus or an optical analyzer for fine patterns.

Example embodiments provide a broadband light source for increasing the collecting efficiency, to thereby increase the intensity of the inspection light of the optical inspector including the broadband light source.

Other example embodiments provide an LPP light source having a plurality of plasma lamps, to thereby increase the wavelength range of the broadband light.

Still other example embodiments provide an optical inspector including the above LPP light source.

According to one or more example embodiments, a large amount of the dissipated light may be collected at the light collector by using the spherical reflector, thereby increasing an intensity of the inspection light that may be illuminated onto the OUT. In addition, according to one or more example embodiments, a plurality of the broadband lights having different bandwidths may be combined into a single inspection light of the optical inspector, thus, the bandwidth of the inspection light may be easily broadened. Therefore, various defects of the OUT may be accurately detected by the optical inspector.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the disclosure. In the claims, means-plus-function clauses are intended to cover the structures described herein as performing the recited function and not only structural equivalents but also equivalent structures. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A broadband light source, comprising:
   an electrodeless lamp to generate broadband light from plasma;
   an elliptical reflector having first and second focuses, the elliptical reflector enclosing a rear portion of the electrodeless lamp positioned at the first focus of the elliptical reflector such that the broadband light is reflected from the elliptical reflector toward a light collector as a collective light;
   a spherical reflector having a spherical center at which the electrodeless lamp is positioned, the spherical reflector enclosing a front portion of the electrodeless lamp such that the broadband light is reflected from the spherical reflector toward the elliptical reflector, the spherical reflector having a path hole through which the collective light passes toward the light collector; and
   a laser irradiator to provide a laser beam to the electrodeless lamp through the path hole of the spherical reflector to generate the plasma in the electrodeless lamp.

2. The broadband light source as claimed in claim 1, wherein the elliptical reflector includes a mirror axis of the elliptical reflector coincides with a major axis of the elliptical reflector such that a first portion of the broadband light emitted from the rear portion of the electrodeless lamp is reflected from the elliptical reflector toward the second focus of the elliptical reflector, and the spherical reflector includes a mirror axis of the spherical reflector coincides with the major axis of the elliptical reflector such that a second portion of the broadband light emitted from the front portion of the electrodeless lamp is reflected from the spherical reflector towards the elliptical reflector.

3. The broadband light source as claimed in claim 2, wherein end portions of the elliptical and the spherical reflectors are on a focal plane intersecting the first focus such that a maximal emitting angle $\alpha_{max}$ of the first portion of the broadband light is 90° clockwise or counterclockwise with respect to the major axis and a maximal focusing angle $\beta_{max}$ of the collective light is defined by equation (1) clockwise or counterclockwise with respect to the major axis,
wherein $$\beta_{max} = \tan^{-1}\left(\frac{b\sqrt{1-\frac{c^2}{a^2}}}{2c}\right) \quad (1)$$

(wherein, 'a' denotes a distance of a prolate vertex, 'b' denotes a distance of an oblate vertex, and 'c' is a focal distance of the elliptical reflector from an origin of a Cartesian coordinate system).

4. The broadband light source as claimed in claim 3, wherein the spherical reflector has a radius R in a range of $$b\sqrt{1-\frac{c^2}{a^2}} \le R \le 2c.$$

5. The broadband light source as claimed in claim 3, wherein the path hole has a maximal cross sectional circle at which the spherical reflector intersects a beam flux of the collective light having the maximal focusing angle $\beta_{max}$.

6. The broadband light source as claimed in claim 2, wherein the laser irradiator includes:
 a laser source to generate the laser beam; and
 an optical selector arranged on the major axis at a position that is spaced apart from the second focus by a gap distance and controlling an optical path of the laser and the collective light.

7. The broadband light source as claimed in claim 6, wherein the laser source is at the second focus and the light collector is spaced apart from the optical selector in a direction perpendicular to the major axis of the elliptical reflector.

8. The broadband light source as claimed in claim 7, wherein the optical selector includes a dichromatic beam splitter that transmits the laser beam toward the elliptical reflector along the major axis and reflects the collective light toward the light collector in a direction perpendicular to the major axis.

9. The broadband light source as claimed in claim 6, wherein the light collector is at the second focus and the laser source is spaced apart from the optical selector in a direction perpendicular to the major axis.

10. The broadband light source as claimed in claim 9, wherein the optical selector includes a dichromatic beam splitter such that the laser beam perpendicular to the major axis is reflected toward the elliptical reflector along the major axis and the collective light passes through the optical selector toward the light collector along the major axis.

11. A broadband light source, comprising:
 a first light source to emit a first broadband light, the first light source having a first electrodeless lamp to generate the first broadband light from a first plasma and a first elliptical reflector that encloses the first electrodeless lamp positioned at a focal point of the first elliptical reflector;
 a second light source to emit a second broadband light, the second light source having a second electrodeless lamp to generate the second broadband light from a second plasma and a second elliptical reflector that encloses the second electrodeless lamp positioned at a focal point of the second elliptical reflector;
 a laser irradiator to irradiate a laser beam to the first and the second electrodeless lamps, thereby generating the first and the second plasma in the first and the second electrodeless lamps, respectively; and
 a path changer to change optical paths of the first and the second broadband lights and the laser such that the first and the second broadband lights travel toward a light collector as a collective light and the laser beam travels toward the first and the second reflectors, respectively.

12. The broadband light source as claimed in claim 11, wherein the first elliptical reflector has a first focus at which the first electrodeless lamp is positioned and a second focus, the first and second focuses defining a first major axis of the first elliptical reflector, the first elliptical reflector having a mirror axis corresponding to the first major axis, and
 the second elliptical reflector has a third focus at which the second electrodeless lamp is positioned and a fourth focus, the third and fourth focuses defining a second major axis of the second elliptical reflector, the second elliptical reflector having a mirror axis corresponding to the second major axis.

13. The broadband light source as claimed in claim 12, wherein the path changer includes a beam splitter located at a cross point of the first and the second major axes such that the path changer is spaced apart from the first and third focuses by a same gap distance, the broadband light source including an optical selector optically connected to both of the laser irradiator and the path changer, the optical selector to selectively transmit one of the laser beam and the collective light.

14. The broadband light source as claimed in claim 13, further comprising a third elliptical reflector facing the first elliptical reflector and enclosing the second focus such that a mirror axis of the third elliptical reflector is a same as that of the first elliptical reflector.

15. The broadband light source as claimed in claim 11, further comprising a first reflective film on a reflection surface of the first elliptical reflector and a second reflective film on a reflection surface of the second elliptical reflector.

16. A broadband light source, comprising:
 a first electrodeless lamp to generate first broadband light from plasma;
 a first elliptical reflector having first and second focuses, the first elliptical reflector enclosing a rear portion of the first electrodeless lamp positioned at the first focus of the first elliptical reflector such that the first broadband light is reflected from the first elliptical reflector toward a light collector as a collective light;
 a second elliptical reflector having a fourth focus and a third focus, the third focus being coincident with the second focus;
 a second electrodeless lamp to generate second broadband light from plasma, the second elliptical reflector enclosing a rear portion of the second electrodeless lamp positioned at the fourth focus of the second elliptical reflector;
 a path changer to change the optical path of the second broadband light such that the second broadband light is focused at the third focus of the second elliptical reflector toward the light collector as collective light; and a laser irradiator to provide a laser beam to the first and second electrodeless lamps.

17. The broadband light source as claimed in claim 16, further comprising a third elliptical reflector facing the first elliptical reflector and enclosing the fourth focus such that a mirror axis of the third elliptical reflector is a same as that of the second elliptical reflector.

* * * * *